US010150792B2

(12) United States Patent
Price et al.

(10) Patent No.: US 10,150,792 B2
(45) Date of Patent: Dec. 11, 2018

(54) BISMUTH-CONTAINING COMPOUNDS, COORDINATION POLYMERS, METHODS FOR MODULATING PHARMACOKINETIC PROPERTIES OF BIOLOGICALLY ACTIVE AGENTS, AND METHODS FOR TREATING PATIENTS

(75) Inventors: John D. Price, Radford, VA (US); Thomas Piccariello, Blacksburg, VA (US); Robert A. Oberlender, Blacksburg, VA (US); Michaela E. Mulhare, Christiansburg, VA (US); Scott B. Palmer, Wilmette, IL (US)

(73) Assignee: Synthonics, Inc., Blacksburg, VA (US)

( * ) Notice: Subject to any disclaimer, the term of this patent is extended or adjusted under 35 U.S.C. 154(b) by 1595 days.

(21) Appl. No.: 12/941,599

(22) Filed: Nov. 8, 2010

(65) Prior Publication Data

US 2012/0115823 A1    May 10, 2012

(51) Int. Cl.
| | | |
|---|---|---|
| C07H 23/00 | (2006.01) | |
| C07F 9/00 | (2006.01) | |
| C08B 37/08 | (2006.01) | |
| C08B 37/00 | (2006.01) | |
| C07C 229/76 | (2006.01) | |

(52) U.S. Cl.
CPC .......... *C07H 23/00* (2013.01); *C07C 229/76* (2013.01); *C07F 9/005* (2013.01); *C08B 37/003* (2013.01); *C08B 37/0084* (2013.01)

(58) Field of Classification Search
CPC ....... C07C 229/76; C07F 9/005; C07H 23/00; C08B 37/003; C08B 37/0084
USPC ...................................................... 514/166
See application file for complete search history.

(56) References Cited

U.S. PATENT DOCUMENTS

| | | | |
|---|---|---|---|
| 6,004,546 | A | 12/1999 | Sachetto |
| 6,565,895 | B2 | 5/2003 | Goddard et al. |
| 7,094,427 | B2 | 8/2006 | Han et al. |
| 7,342,131 | B2 | 3/2008 | Xiang et al. |
| 2002/0081340 | A1 | 6/2002 | Goddard et al. |
| 2002/0120165 | A1 | 8/2002 | Zaworotko et al. |
| 2003/0224006 | A1 | 12/2003 | Zaworotko et al. |
| 2004/0156893 | A1 | 8/2004 | Klein et al. |
| 2006/0141054 | A1 | 6/2006 | Piccariello |
| 2007/0026078 | A1 | 2/2007 | Almarsson et al. |
| 2007/0059356 | A1 | 3/2007 | Almarsson et al. |
| 2007/0225366 | A1 | 9/2007 | Xiang et al. |
| 2008/0221211 | A1 | 9/2008 | Streeter |
| 2008/0260824 | A1 | 10/2008 | Nangia et al. |
| 2009/0143338 | A1 | 6/2009 | Piccariello |
| 2009/0209046 | A1 | 8/2009 | Moulton et al. |
| 2009/0227446 | A1 | 9/2009 | Chang et al. |
| 2010/0209354 | A1 | 8/2010 | Horcajada-Cortes et al. |
| 2010/0226991 | A1 | 9/2010 | Horcajada-Cortes et al. |
| 2010/0273642 | A1 | 10/2010 | Chang et al. |
| 2010/0311701 | A1 | 12/2010 | Almarsson et al. |
| 2011/0052650 | A1 | 3/2011 | Morris et al. |
| 2011/0086911 | A1 | 4/2011 | Andrews et al. |

FOREIGN PATENT DOCUMENTS

| | | |
|---|---|---|
| GB | 2442317 A | 4/2008 |
| JP | 2004-500378 A | 1/2004 |
| JP | 2009-512728 A | 3/2009 |
| WO | WO 97/19949 A1 | 6/1997 |
| WO | WO 01/56547 A2 | 8/2001 |
| WO | WO 03/074474 A2 | 9/2003 |
| WO | WO 2007/050181 A2 | 5/2007 |
| WO | WO 2008/079404 A3 | 7/2008 |
| WO | WO 2009/144558 A1 | 12/2009 |

OTHER PUBLICATIONS

Abuznaid, M.; Sallam, A-S.; Hamdan, I.; Al-Hussaini, M.; Bani-Jaber, A. "Diclofenac-Bismuth Complex: Synthesis, Physicochemical, and Biological Evaluation," *Drug Dev. Ind. Pharm.*, 2008, 34, 434-444.
Andrews, P.C.; Deacon, G.B.; Junk, P.C.; Kumar, I.; Silberstein, M. "Synthetic and Structural Comparisons of Bismuth(III) Carboxylates Synthesised Under Solvent-Free and Reflux Conditions," *Dalton Trans.*, 2006, 4852-4858.
Andrews, P.C.; Ferrero, R.L.; Junk, P.C.; Kumar, I.; Luu, Q.; Nguyen, K.; Taylor, J.W. "Bimuth(III) Complexes Derived From Non-Steroidal Anti-Inflammatory Drugs and Their Activity Against *Helicobacter pylori*," *Dalton Trans.*, 2010, 39, 2861-2868.
Bet, L.; Bareggi, S.R.; Pacei, F.; Bondiolotti, G.; Meola, G.; Schapira, A.H.V. "Bimodal Administration of Entacapone in Parkinson's Disease Patients Improves Motor Control," *Eur. J. Neurol.*, 2008, 15, 268-273.
Bhattacharya, P.K. "Chapter 2—Thermodynamic and Kinetic Properties of Metal Complexes," *Metal Ions in Biochemistry, Alpha Science International Ltd.*, 2005, Harrow, U.K., 16-65.
Birkmayer W.; Hornykiewicz, O. "Der L-3,4-Dioxyphenylalanine (=DOPA)-Effekt bei der Parkinson-akinese," *Wien. Kim. Wochenschr.*, 1961, 73, 787-788 (with English abstract as published in Current Contents, 1982, 14, 22).
Bodor, N.; Sloan, K.B.; Higuchi, T; Sasahara, K. "Improved Delivery Through Biological Membranes. 4. Prodrugs of L-Dopa," *J. Med. Chem.*, 1977, 20, 1435-1445.
Briand, G.G.; Burford, N. "Bismuth Compounds and Preparations with Biological or Medicinal Relevance," *Chem. Rev.*, 1999, 99, 2601-2657.

(Continued)

*Primary Examiner* — My-Chau T. Tran
(74) *Attorney, Agent, or Firm* — Brinks Gilson & Lione; Ryan L. Marshall; Bryan Richardson

(57) ABSTRACT

Bismuth-containing compounds include bismuth and a biologically active agent coordinated to the bismuth. The biologically active agent includes at least one heteroatom configured for coordination with the bismuth. Coordination polymers include a polymer matrix that contains a bismuth-containing compound. Methods for modulating a pharmacokinetic property of a biologically active agent include coordinating the biologically active agent to bismuth to form a bismuth-containing compound, and administering the bismuth-containing compound orally to a patient. Methods for treating Parkinson's disease, methods for treating hypothyroidism, methods for treating ulcerative colitis, and methods for treating cancer each include administering a bismuth-containing compound to a patient.

16 Claims, 8 Drawing Sheets

(56) References Cited

OTHER PUBLICATIONS

Briand, G.G.; Burford, N.; Eelman, M.D.; Aumeerally, N.; Chen, L.; Cameron, T.S.; Robertson, K.N. "Identification, Isolation, and Characterization of Cysteinate and Thiolactate Complexes of Bismuth," *Inorg. Chem.*, 2004, 43, 6495-6500.

Bunevičius, R.; Kažanavičius, G.; Žalinkevičius, R.; Prange, Jr., A.J. "Effects of Thyroxine as Compared With Thyroxine Plus Triiodothyronine in Patients With Hypothyroidism," *N. Engl. J. Med.*, 1999, 340, 424-429.

Butterworth, J.R. "Chemoprevention of Colorectal Cancer in Inflammatory Bowel Disease," *Dig. Liver Dis.*, 2009, 41, 338-339.

Canevari, M.; Castagliuolo, I.; Brun, P.; Cardin, M.; Schiavon, M.; Pasut, G.; Veronese, F.M. "Poly(ethylene glycol)-Mesalazine Conjugate for Colon Specific Delivery," *Int. J. Pharm.*, 2009, 368, 171-177.

Celi, F.S.; Zemskova, M.; Linderman, J.D.; Babar, N.I.; Skarulis, M.C.; Csako, G.; Wesley, R.; Costello, R.; Penzak, S.R.; Pucino, F. "The Pharmacodynamic Equivalence of Levothyroxine and Liothyronine: A Randomized, Double Blind, Cross-Over Study in Thyroidectomized Patients," *Clin. Endocrinol.*, 2010, 72, 709-715.

Chang, C.J.; Lippard, S.J. "Zinc Metalloneurochemistry: Physiology, Pathology, and Probes," *Met. Ions Life Sci.*, 2006, 1, 321-370.

Cieślak M.; Komoszyński, M.; Wojtczak, A. "Adenosine $A_{2A}$ Receptors in Parkinson's Disease Treatment," *Purinergic Signal.*, 2008, 4, 305-312.

Coghill, S.B. "Experimental Studies Using Colloidal Bismuth Subcitrate: Possible Modes of Action," *Proceedings of an International Symposium Organized Under the Auspices of the University of Cairo: In Pathogenesis and the Treatment of Peptic Ulcer Disease*; Axon, A.T.R. (ed.), *Excerpta Medica*, Amsterdam, 1985; 7-12 (9 pages).

Cooper, D.S. "Combined T4 and T3 Therapy—Back to the Drawing Board," *JAMA*, 2003, 290, 3002-3004.

Cotzias, G.C.; Van Woert, M.H.; Schiffer, L.M. "Aromatic Amino Acids and Modification of Parkinsonism," *N. Engl. J. Med.*, 1967, 276, 374-379.

Denora, N.; Laquintana, V.; Lopedota, A.; Serra, M.; Dazzi, L.; Biggio, G.; Pal, D.; Mitra, A.K.; Latrofa, A.; Trapani, G.; Liso, G. "Novel L-Dopa and Dopamine Prodrugs Containing a 2-Phenyl-Imidazopyridine Moiety," *Pharm. Res.*, 2007, 24, 1309-1324.

Desai, B.S.; Monohan, A.J.; Carvey, P.M.; Hendey, B. "Blood-Brain Barrier Pathology in Alzheimer's and Parkinson's Disease: Implications for Drug Therapy," *Cell Transplantation*, 2007, 16, 285-299.

Di Stefano, A.; Sozio, P.; Cerasa, L.S. "Antiparkinson Prodrugs," *Molecules*, 2008, 13, 46-68.

Eaden, J. "Review Article: the Data Supporting a Role for Aminosalicylates in the Chemoprevention of Colorectal Cancer in Patients With Inflammatory Bowel Disease," *Aliment. Pharmacol. Ther.*, 2003, 18 (Suppl. 2), 15-21.

Escobar-Morreale, H.F.; Escobar del Rey, F.; Obregón, M.J.; Morreale de Escobar, G. "Only the Combined Treatment With Thyroxine and Triiodothyronine Ensures Euthyroidism in All Tissues of the Thyroidectomized Rat," *Endocrinology*, 1996, 137, 2490-2502.

Escobar-Morreale, H.F.; Botella-Carretero, J.I.; Escobar del Rey, F.; Morreale de Escobar, G. "Review: Treatment of Hypothyroidism With Combinations of Levothyroxine Plus Liothyronine," *J. Clin. Endocrinol. Metab.*, 2005, 90, 4946-4954.

Fariello, R.G.; Lieberman, A. "Present and Future Approaches to Parkinson Disease: From Molecular Insights to New Therapeutic Avenues," *Neurology*, 2006, 67 (Suppl. 2), S1-S4.

Farwell, A.P.; Braverman, L.E. "Chapter 56—Thyroid and Antithyroid Drugs," *Goodman and Gilman's the Pharmacological Basis of Therapeutics*, J. G. Hardman, L. E. Limbird, P. B. Molinoff, R. W. Ruddon and A. G. Gilman, 1996, New York, McGraw-Hill, 1383-1401.

Fernández, C.; Nieto, O.; Rivas, E.; Montenegro, G.; Fontenla, J.A.; Fernandez-Mayoralas, A. "Synthesis and Biological Studies of Glycosyl Dopamine Derivatives as Potential Antiparkinsonian Agents," *Carbohydr. Res.*, 2000, 327, 353-365.

Fish, L.H.; Schwartz, H.L.; Cavanaugh, J.; Steffes, M.W.; Bantle, J.P.; Oppenheimer, J.H. "Replacement Dose, Metabolism, and Bioavailability of Levothyroxine in the Treatment of Hypothyroidism: Role of Triiodothyronine in Pituitary Feedback in Humans," *N. Engl. J. Med.*, 1987, 316, 764-770.

Fraga, S.; Serrão, M.P.; Soares-da-Silva, P. "L-Type Amino Acid Transporters in Two Intestinal Epithelial Cell Lines Function as Exchangers With Neutral Amino Acids," *J. Nutr.*, 2002, 132, 733-738.

Ge, R.; Sun, H. "Bioinorganic Chemistry of Bismuth and Antimony: Target Sites of Metallodrugs," *Acc. Chem. Res.*, 2007, 40, 267-274.

Giannini, E.G.; Kane, S.V.; Testa, R.; Savarino, V. "5-ASA and Colorectal Cancer Chemoprevention in Inflammatory Bowel Disease: Can We Afford to Wait for 'Best Evidence'?" *Dig. Liver Dis.*, 2005, 37, 723-731.

Gionchetti, P.; Rizzello, F.; Venturi, A.; Ferretti, M.; Brignola, C.; Peruzzo, S.; Belloli, C.; Poggioli, G.; Miglioli, M.; Campieri, M. "Long-Term Efficacy of Bismuth Carbomer Enemas in Patients With Treatment-Resistant Chronic Pouchitis," *Aliment. Pharmacol. Ther.*, 1997, 11, 673-678.

Goldenberg, M.M.; Honkomp, L.J.; Burrous, S.E.; Castellion, A.W. "Protective Effect of Pepto-Bismol Liquid on the Gastric Mucosa of Rats," *Gastroenterology*, 1975, 69, 636-640.

Gow, S.M.; Caldwell, G.; Toft, A.d.; Seth, J.; Hussey, A.J.; Sweeting, V.M.; Beckett, G.J. "Relationship Between Pituitary and Other Target Organ Responsiveness in Hypothyroid Patients Receiving Thyroxine Replacement," *J. Clin. Endocrinol. Metab.*, 1987, 64, 364-370.

Hamada, Y.Z.; Rogers, C. "Interaction of L-3,4-dihydroxyphenylalanine (L-DOPA) as a Coordinating Ligand With a Series of Metal Ions; Reaction of L-DOPA," *J. Coord. Chem.*, 2007, 60, 2149-2163.

Hauser, R.A. "Levodopa: Past, Present, and Future," *Eur. Neurol.*, 2009, 62, 1-8.

Hays, M.T. "Thyroid Hormone and the Gut," Endocr. Res., 1988, 14, 203-224.

Hennemann, G.; Docter, R.; Friesema, E.C.H.; de Jong, M.; Krenning, E.P.; Visser, T.J. "Plasma Membrane Transport of Thyroid Hormones and Its Role in Thyroid Hormone Metabolism and Bioavailability," *Endocr. Rev.*, 2001, 22, 451-476.

Hennemann, G.; Docter, R.; Visser, T.J.; Postema, P.T.; Krenning, E.P. "Thyroxine Plus Low-Dose, Slow-Release Triiodothyronine Replacement in Hypothyroidism: Proof of Principle," *Thyroid*, 2004, 14, 271-275.

Hovgaard, L.; Brøndsted, H. "Dextran Hydrogels for Colon-Specific Drug Delivery," *J. Control. Release*, 1995, 36, 159-166.

Huber, J.D.; Egleton, R.D.; Davis, T.P. "Molecular Physiology and Pathophysiology of Tight Junctions in the Blood-Brain Barrier," *Trends Neurosci.*, 2001, 24, 719-725.

Jin, Y.; Ling, P.X.; He, Y.L.; Chen, L.; Chen, J.Y.; Zhang, T.M. "Preparation, Characterization and Anti-*Helicobacter pylori* Activity of $Bi^{3+}$-hyaluronate Complex," *Carbohydrate Polymers*, 2008, 74, 50-58.

Jung, Y.J.; Lee, J.S.; Kim, Y.M. "Synthesis and in Vitro/in Vivo Evaluation of 5-Aminosalicyl-Glycine as a Colon-Specific Prodrug of 5-Aminosalicylic Acid," *J. Pharm. Sci.*, 2000, 89, 594-602.

Kalala, W.; Kinget, R.; Van den Mooter, G.; Samyn, C. "Colonic Drug-Targeting: In Vitro Release of Ibuprofen From Capsules Coated With Poly(Ether-Ester) Azopolymers," *Int. J. Pharm.*, 1996, 139, 187-195.

Kane, S.V. "Systematic Review: Adherence Issues in the Treatment of Ulcerative Colitis," *Aliment. Pharmacol. Ther.*, 2006, 23, 577-585.

Kao, H.D.; Traboulsi, A; Itoh, S.; Dittert, L.; Hussain, A. "Enhancement of the Systemic and CNS Specific Delivery of L-Dopa by the Nasal Administration of its Water Soluble Prodrugs," *Pharm. Res.*, 2000, 17, 978-984.

Karagozian, R.; Burakoff, R. "The Role of Mesalamine in the Treatment of Ulcerative Colitis," *Ther. Clin. Risk Manag.*, 2007, 3, 893-903.

Killian, D.M.; Chikhale, P.J. "Predominant Functional Activity of the Large, Neutral Amino Acid Transporter (LAT1) Isoform at the Cerebrovasculature," *Neurosci. Lett.*, 2001, 306, 1-4.

(56) References Cited

OTHER PUBLICATIONS

Kim, Y-H.; Kim, M.H.; Kim, B.J.; Kim, J.J.; Chang, D.K.; Son, H.J.; Rhee, P-L.; Rhee, J.C. "Inhibition of Cell Proliferation and Invasion in a Human Colon Cancer Cell Line by 5-Aminosalicylic Acid," *Dig. Liver Dis.*, 2009, 41, 328-337.

King, R.B. "Chemical Bonding Topology of Ternary Transition Metal-Centered Bismuth Cluster Halides: From Molecules to Metals," *Inorg. Chem.*, 2003, 42, 8755-8761.

Klausner, E.A.; Lavy, E.; Barta, M.; Cserepes, E.; Friedman, M.; Hoffman, A. "Novel Gastroretentive Dosage Forms: Evaluation of Gastroretentivity and Its Effect on Levodopa Absorption in Humans," *Pharm. Res.*, 2003, 20, 1466-1473.

Konishi, Y.; Shimizu, M. "Transepithelial Transport of Ferulic Acid by Monocarboxylic Acid Transporter in Caco-2 Cell Monolayers," *Biosci. Biotechnol. Biochem.*, 2003, 67, 856-862.

Koo, J.; Ho, J.; Lam, S.K.; Wong, J.; Ong, G.B. "Selective Coating of Gastric Ulcer by Tripotassium Dicitrato Bismuthate in the Rat," *Gastroenterology*, 1982, 82, 864-870.

Kopeček, J.; Kopečková, P.; Brønsted, H.; Rathi, R.; Řihová, B.; Yeh, P.-Y.; Ikesue, K. "Polymers for Colon Specific Drug Delivery," *J. Control. Release*, 1992, 19, 121-130.

Kopeček, J. "The Potential of Water-Soluble Polymeric Carriers in Targeted and Site-Specific Drug Delivery," *J. Control. Release*, 1990, 11, 279-290.

Kwak, S.-Y.; Noh, J.-M.; Park, S.-H.; Byun, J.-W.; Choi, H.-R.; Park, K.-C.; Lee, Y.-S. "Enhanced Cell Permeability of Kojic Acid-Phenylalanine Amide With Metal Complex," *Biorganic Med. Chem. Lett.*, 2010, 20, 738-741.

Laulicht, B.; Cheifetz, P.; Tripathi, A.; Mathiowitz, E. "Are in Vivo Gastric Bioadhesive Forces Accurately Reflected by in Vitro Experiments?" *J. Control. Release*, 2009, 134, 103-110.

Leboeuf, R.; Perron, P.; Carpentier, A.C.; Verreault, J.; Langlois, M.-F. "L-$T_3$ Preparation for Whole-Body Scintigraphy: A Randomized-Controlled Trial." *Clin. Endocrinol.*, 2007, 67, 839-844.

Lennernäs, H.; Nilsson, D; Aquilonius, S.-M.; Ahrenstedt, Ö.; Knutson, L.; Paalzow, L.K. "The Effect of L-Leucine on the Absorption of Levodopa, Studied by Regional Jejunal Perfusion in Man," *Br. J. Clin. Pharmac.*, 1993, 35, 243-250.

Leonard, J.L. "Regulation of T3 Production in the Brain," *Acta. Med. Austriaca*, 1992, 19, 5-8.

LeWitt, P.A.; Nyholm, D. "New Developments in Levodopa Therapy," *Neurology*, 2004, 62 (Suppl. 1), S9-S16.

Li, W.; Jin, L.; Zhu, N.; Hou, X.; Deng, F.; Sun, H. "Structure of Colloidal Bismuth Subcitrate(CBS) in Dilute HCl: Unique Assembly of Bismuth Citrate Dinuclear Units ([Bi(cit)$_2$Bi]$^{2-}$)," *J. Am. Chem. Soc.*, 2003, 125, 12408-12409.

Lichtenstein, G.R.; Kamm, M.A. "Review Article: 5-Aminosalicylate Formulations for the Treatment of Ulcerative Colitis—Methods of Comparing Release Rates and Delivery of 5-Aminosalicylate to the Colonic Mucosa," *Aliment. Pharmacol. Ther.*, 2008, 28, 663-673.

Linert, W.; Jameson, G.N.L.; Jameson, R.F.; Jellinger, K.A. "The Chemical Interplay Between Catecholamines and Metal Ions in Neurological Diseases," *Met. Ions Life Sci.*, 2006, 1, 281-320.

Lippard, S.J.; Berg, J.M. "Principles of Bioorganic Chemistry," University Science Books, Mill Valley, CA, 1994, 22.

Manfredini, S; Pavan, B; Vertuani, S; Scaglianti, M; Compagnone, D; Biondi, C; Scatturin, A; Tanganelli, S; Ferraro, L; Prasad, P; Dalpiaz, A. "Design, Synthesis and Activity of Ascorbic Acid Prodrugs of Nipecotic, Kynurenic and Diclophenamic Acids, Liable to Increase Neurotropic Activity," *J. Med. Chem.*, 2002, 45, 559-562.

Mercuri, N.B.; Bernardi, G. "The 'Magic' of L-dopa: Why is it the Gold Standard Parkinson's Disease Therapy?" *Trends Pharmacol. Sci.*, 2005, 26, 341-344.

Milojevic, S.; Newton, J.M.; Cummings, J.H.; Gibson, G.R.; Bothman, R.L.; Ring, S.G.; Allwood, M.C.; Stockham, M. "Amylose, the New Perspective in Oral Drug Delivery to the Human Large Intestine," *S.T.P. Pharma Sci.*, 1995, 5, 47-53.

Misu, Y.; Kitahama, K.; Goshima, Y. "L-3,4-Dihydroxyphenylalanine as a Neurotransmitter Candidate in the Central Nervous System," *Pharmacol. Ther.*, 2003, 97, 117-137.

Miyazaki, I.; Asanuma, M.; Hozumi, H.; Miyoshi, K.; Sogawa, N. "Protective Effects of Metallothionein Against Dopamine Quinone-Induced Dopaminergic Neurotoxicity," *FEBS Lett.*, 2007, 581, 5003-5008.

Mouzas, I. A.; Papavassiliou, E.; Koutroubakis, I. "Chemoprevention of Colorectal Cancer in Inflammatory Bowel Disease? A Potential Role for Folate," *Ital. J. Gastroenterol. Hepatol.*, 1998, 30, 421-425.

Nutt, J.G. "Review: Continuous Dopaminergic Stimulation: Is it the Answer to the Motor Complications of Levodopa?" *Mov. Disord.*, 2007, 22, 1-9.

Nwokolo, C.U.; Mistry, P.; Pounder, R.E. "The Absorption of Bismuth and Salicylate From Oral Doses of Pepto-Bismol (Bismuth Salicylate)," *Aliment. Pharmacol. Therap.*, 1990, 4, 163-169.

Nyholm, D. "Pharmacokinetic Optimisation in the Treatment of Parkinson's Disease: An Update," *Clin. Pharmacokinet*, 2006, 45, 109-136.

Nyholm, D. "The Rationale for Continuous Dopaminergic Stimulation in Advanced Parkinson's Disease," *Parkinsonism Relat. Disord.*, 2007, 13, S13-S17.

Nyholm, D.; Lennernäs, H. "Irregular Gastrointestinal Drug Absorption in Parkinson's Disease," *Expert Opin. Drug Metab. Toxicol.*, 2008, 4, 193-203.

Obeso, J.A.; Rodriguez-Oroz, M.C.; Chana, P.; Lera, G.; Rodriguez, M.; Olanow, C.W. "The Evolution and Origin of Motor Complications in Parkinson's Disease," *Neurology*, 2000, 55 (Suppl. 4), S13-S23.

Olanow, C.W. "Levodopa/Dopamine Replacement Strategies in Parkinson's Disease—Future Directions," *Movement Disorders*, 2008, 23 (Suppl. 3), S613-S622.

Olanow, C.W.; Obeso, J.A.; Stocchi, F. "Drug Insight: Continuous Dopaminergic Stimulation in the Treatment of Parkinson's Disease," *Nat. Clin. Pract. Neurol.*, 2006, 2, 382-392.

Olanow, C.W.; Obeso, J.A.; Stocchi, F. "Continuous Dopamine-Receptor Treatment of Parkinson's Disease: Scientific Rationale and Clinical Implications," *Lancet. Neurol.*, 2006, 5, 677-687.

Peeters, R.; Kinget, R. "Film-Forming Polymers for Colonic Drug Delivery: I. Synthesis and Physical and Chemical Properties of Methyl Derivatives of Eudragit S," *Int. J. Pharm.*, 1993, 94, 125-134.

Peterson, T.C.; Cleary, C.E.; Shaw, A.M.; Malatjalian, D.A.; Veldhuyzen van Zanten, S.J.O. "Therapeutic Role for Bismuth Compounds in TNBS-Induced Colitis in the Rat." *Dig. Dis. Sci.*, 2000, 45, 466-473.

Pilo, A.; Iervasi, G.; Vitek, F.; Ferdeghini, M.; Cazzuola, F.; Bianchi, R. "Thyroidal and Peripheral Production of 3,5,3'-Triiodothyronine in Humans by Multicompartmental Analysis," *Am. J. Physiol.*, 1990, 258, E715-E726.

Ponto, L.L.B.; Schoenwald, R.D. "Furosemide (frusemide). A Pharmacokinetic/ Pharmacodynamic Review (Part I)," *Clin. Pharmacokinet.*, 1990,18, 381-408.

Pullan, R.D.; Ganesh, S.; Mani, V.; Morris, J.; Evans, B.K.; Williams, G.T.; Rhodes, J. "Comparison of Bismuth Citrate and 5-Aminosalicylic Acid Enemas in Distal Ulcerative Colitis: A Controlled Trial," *Gut*, 1993, 34, 676-679.

Rajan, K.S.; Manian, A.A.; Davis, J.M.; Dekirmenjian, H. "Metal Chelates of L-DOPA for Improved Replenishment of Dopaminergic Pools," *Brain. Res.*, 1976, 107, 317-331.

Rao, N.; Brown, P.W.; Yerino, P.; Chang, J.; Hwang, K.-K. "Comparative Absorption of Bismuth in Sprague-Dawley Rats Following Oral Administration of Preparations Containing Bismuth Sucrose Octasulfate, Bismuth Subsalicylate, and Bismuth Subcitrate," *Biopharm. Drug Dispos.*, 1997, 18, 1-8.

Riley, D.; Lang, A.E. "Practical Application of a Low-Protein Diet for Parkinson's Disease," *Neurology*, 1988, 38, 1026-1031.

Roti, E.; Minelli, R.; Gardini, E.; Braverman, L.E. "The Use and Misuse of Thyroid Hormone," *Endocr. Rev.*, 1993, 14, 401-423.

Rubinstein, A.; Radai, R.; Ezra, M.; Pathak, S.; Rokem, J.S. "In Vitro Evaluation of Calcium Pectinate: A Potential Colon-Specific Drug Delivery Carrier," *Pharm. Res.*, 1993, 10, 258-263.

(56) References Cited

OTHER PUBLICATIONS

Saffran, M.; Field, J.B.; Peña, J.; Jones, R.H.; Okuda, Y. "Oral Insulin in Diabetic Dogs," *J. Endocrinol.*, 1991, 131, 267-278.
Sakuma, S.; Lu, Z.-R.; Kopečková, P.; Kopeček, J. "Biorecognizable HPMA Copolymer-Drug Conjugates for Colon-Specific Delivery of 9-Aminocamptothecin," *J. Control. Release*, 2001, 75, 365-379.
Sandborn, W.J. "Oral 5-ASA Therapy in Ulcerative Colitis: What are the Implications of the New Formulations?" *J. Clin. Gastroentero.*, 2008, 42, 338-344.
Srivastava, E.D.; Swift, G.L.; Wilkinson, S.; Williams, G.T.; Evans, B.K.; Rhodes, J. "Tripotassium Dictrato Bismuthate Enemas in the Treatment of Ulcerative Proctitis," *Aliment. Pharmacol. Therap.*, 1990, 4, 557-581.
Stocchi, F. "The Levodopa Wearing-off Phenomenon in Parkinson's Disease: Pharmacokinetic Considerations," *Expert Opin. Pharmacother.*, 2006, 7, 1399-1407.
Stocchi, F.; Tagliati, M.: Olanow, C.W. "Treatment of Levodopa-Induced Motor Complications," *Movement Disorders*, 2008, 23 (Suppl. 3), S599-S612.
Stowe, R.; Ives, N.; Clarke, C.E.; van Hilten; Ferreira, J.; Hawker, R.J.; Shah, L.; Wheatley, K.; Gray, R. "Dopamine Agonist Therapy in Early Parkinson's Disease (Review)," *Cochrane Database Syst. Rev.*, 2008, (2):CD006564. DOI: 10.1002/14651858.CD006564. pub2, 92 pages.
Streubel, A.; Siepmann, J.; Bodmeier, R. "Drug Delivery to the Upper Small Intestine Window Using Gastroretentive Technologies," *Curr. Opin. Pharmacol.*, 2006, 6, 501-508.
Sun, H.; Li, H.; Sadler, P.J., "The Biological and Medicinal Chemistry of Bismuth," *Chem. Ber./Recueil*, 1997, 130, 669-681.
Suzuki, H.; Matano, Y. (eds.) "Organobismuth (III) Compounds" in *Organobismuth Chemistry*, Elsevier Science BV, Amsterdam, 2001, 21-245.
Tønnesen, H.H.; Karlsen, J. "Alginate in Drug Delivery Systems," *Drug Development and Industrial Pharmacy*, 2002, 28, 621-630.
Touitou, E.; Rubinstein, A. "Targeted Enteral Delivery of Insulin to Rats," *Int. J. Pharm.*, 1986, 30, 95-99.
Tsuji, A. "Small Molecular Drug Transfer Across the Blood-Brain Barrier via Carrier-Mediated Transport Systems," *NeuroRx*, 2005, 2, 54-62.
Uldry, M.; Ibberson, M.; Hosokawa, M.; Thorens, B. "GLUT2 is a High Affinity Glucosamine Transporter," *FEBS Lett.*, 2002, 524, 199-203.
Van den Mooter, G.; Samyn, C.; Kinget, R. "Azo Polymers for Colon-Specific Drug Delivery," *Int. J. Pharm.*, 1992, 87, 37-46.
Van den Mooter, G.; Samyn, C.; Kinget, R. "Azo Polymers for Colon-Specific Drug Delivery. II: Influence of the Type of Azo Polymer on the Degradation by Intestinal Microflora," *Int. J. Pharm.*, 1993, 97, 133-139.
Visser, T.J.; Leonard, J.L.; Kaplan, M.M.; Larsen, P.R. "Kinetic Evidence Suggesting Two Mechanisms for Iodothyronine 5'-Deiodination in Rat Cerebral Cortex," *Proc. Natl. Acad. Sci. USA*, 1982, 79, 5080-5084.
Waite, J.H. "Reverse Engineering of Bioadhesion in Marine Mussels," *Ann. NY Acad. Sci.*, 1999, 875, 301-309.
Wang, M-L.; Chang, R.-B.; Liu, D.-S. "Synthesis and antitumour activity of metal complexes of bacteriochlorophyll," *Acta Pharmaceutica Sinica*, 2005, 40, 920-923.
Wang, Y.; Fice, D.S.; Yeung, P.K.F. "A Simple High-Performance Liquid Chromatography Assay for Simultaneous Determination of Plasma Norepinephrine, Epinephrine, Dopamine and 3,4-Dihydroxyphenyl Acetic Acid," *J. Pharm. Biomed. Anal.*, 1999, 21, 519-525.
Yang, N.; Sun, H. "Biocoordination Chemistry of Bismuth: Recent Advances," *Coord. Chem. Rev.*, 2007, 251, 2354-2366.
Jones, C.E.; Taylor, P.J.; McEwan, A.G.; Hanson, G.R. "Spectroscopic Characterization of Copper (II) Binding to the Immunosuppressive Drug Mycophenolic Acid," *J. Am. chem.. Soc.*, 2006, 128, 9378-9386.
Ma, Z.; Han, S.; Kravtsov, V.C.; Moulton, B. "Conformational Isomerism and Hydrogen-Bonded Motifs of Anion Assisted Supramolecular Self-Assemblies Using Cu/Co Salts and Pyridine-4-Acetamide," *Inorganica Chimica Acta*, 2010, 363, 387-394.
Ma, Z.; Hopson, R.; Cai, C.; Han, S.; Moulton, B. "Modifying Lipophilicities of Zn(II) Coordination Species by Introduction of Ancillary Ligands: A Supramolecular Chemistry Approach," *Crystal Growth & Design*, 2010, 10, 2376-2381.
Ma, Z.; Moulton, B. "Mixed-Ligand Coordination Species: A Promising Approach for 'Second-Generation' Drug Development," *Crystal Growth & Design*, 2007, 7, 196-198.
Ma, Z.; Moulton, B. "Recent Advances of Discrete Coordination Complexes and Coordination Polymers in Drug Delivery," *Coordination Chemistry Reviews*, 2011, Article in Press, 19 pages.
Ma, Z.; Moulton, B. "Supramolecular Medicinal Chemistry: Mixed-Ligand Coordination Complexes," Molecular Pharmaceutics, 2007, 4, 373-385.
Miller, S.; Heurtaux, D.; Baati, T.; Horcajada, P.; Grenech, J-M.; Serre, C. "Biodegradable Therapeutic MOFs for the Delivery of Bioactive Molecules," Chem. Commun., 2010, 46, 4526-4528.
Moulton, B.; Zaworotko, M.J. "From Molecules to Crystal Engineering: Supramolecular Isomerism and Polymorphism in Network Solids," Chem. Rev., 2001, 101, 1629-1658.
Kürthy, L.; Müller, H.; Biochemische Zeitschrift 1924, 149th vol. 235-238.
Second Office Action for related Chinese Application No. 201180063098.X, dated Feb. 28, 2015 (18 pages).
Andrews, Philip C., et al., "Bismuth(III) 5-sulfosalicylate complexes: structure, solubility and activity against *Helicobacter pylori*," *Dalton Trans.*, pp. 6377-6384 (2009).
Examination Report from corresponding Canadian Patent Application No. 2,816,895, dated Feb. 18, 2014 (2 pages).
Supplementary European Search Report for corresponding European Patent Application No. 11839065.7, dated Oct. 27, 2014 (5 pages).

BISMUTH-CONTAINING COMPOUNDS, COORDINATION POLYMERS, METHODS FOR MODULATING PHARMACOKINETIC PROPERTIES OF BIOLOGICALLY ACTIVE AGENTS, AND METHODS FOR TREATING PATIENTS

FEDERALLY SPONSORED RESEARCH OR DEVELOPMENT

This invention was made with government support under Grant No. 1R43NS065572-01A1 awarded by National Institutes of Health. The government has certain rights in the invention.

TECHNICAL FIELD

The present teachings relate generally to bismuth-containing compounds, methods for their therapeutic use in the treatment of patients, and methods for modulating the pharmacokinetic properties of biologically active agents.

BACKGROUND

Frequently, the therapeutic efficacy of a promising pharmaceutical agent is undermined as a result of one or more unfavorable pharmacokinetic properties exhibited by the agent when it is administered in vivo to a patient. Indeed, achieving an optimum balance between a drug's various pharmacokinetic properties remains a significant challenge within the pharmaceutical field.

By way of example, the absorption kinetics of a drug (e.g., the degree to which and the duration of time over which a drug is absorbed by a patient), the inter- and intra-subject variability of a drug's absorption, the plasma concentration of a drug and its steadiness over time, the occurrence of dangerous concentration surges in a drug's maximum concentration ($C_{max}$), the general bioavailability of a drug, the toxicity of a drug, and the like are all factors in determining the therapeutic utility and efficacy of prospective drug candidates. If an acceptable balance in these and other parameters cannot be achieved and/or if the cost/benefit ratio associated with the drug's use is deemed inadequate, a drug candidate may be discarded regardless of its promise in treating a particular malady.

Unfavorable pharmacokinetic properties can also limit the use, safety or effectiveness of marketed drugs. Representative drugs that—notwithstanding their established or presumptive efficacies in treating certain disorders—are deemed to be lacking with respect to one or more of their pharmacokinetic properties include but are not limited to levodopa (LD) in the treatment of Parkinson's disease (PD), 3,5,3'-triiodothyronine (T3) in the treatment of hypothyroidism, mesalamine in the treatment of ulcerative colitis (UC), and dichloroacetate (DCA) in the treatment of cancer.

In short, the ability to modulate a pharmacokinetic property of a biologically active agent (e.g., to provide extended release, improved bioavailability, enhanced absorption, reduced variability, an extended therapeutic window, safe plasma levels, and the like) would be highly desirable.

SUMMARY

The scope of the present invention is defined solely by the appended claims, and is not affected to any degree by the statements within this summary.

A first bismuth-containing compound includes bismuth and a biologically active agent coordinated to the bismuth. The biologically active agent includes at least one heteroatom configured for coordination with the bismuth.

A second bismuth-containing compound includes bismuth, a second metal that is not bismuth, and a biologically active agent coordinated to each of the bismuth and the second metal. The biologically active agent includes at least two heteroatoms, each of which is independently configured for coordination with the bismuth and the second metal.

A coordination polymer includes a polymer matrix that contains a bismuth-containing compound. The bismuth-containing compound includes bismuth and a biologically active agent coordinated to the bismuth. The biologically active agent includes at least one heteroatom configured for coordination with the bismuth.

A method for modulating a pharmacokinetic property of a biologically active agent includes coordinating the biologically active agent to bismuth to form a bismuth-containing compound, and administering the bismuth-containing compound orally to a patient. A pharmacokinetic property of the bismuth-containing compound is modulated relative to that of the biologically active agent in an uncoordinated state.

A method for treating Parkinson's disease includes administering a bismuth-containing compound orally to a patient, wherein the bismuth-containing compound includes bismuth and levodopa coordinated to the bismuth.

A method for treating hypothyroidism includes administering a bismuth-containing compound orally to a patient, wherein the bismuth-containing compound comprises bismuth and triiodothyronine coordinated to the bismuth.

A method for treating ulcerative colitis includes administering a bismuth-containing compound orally and/or rectally to a patient, wherein the bismuth-containing compound comprises bismuth and mesalamine coordinated to the bismuth.

A method for treating cancer includes administering a bismuth-containing compound orally to a patient, wherein the bismuth-containing compound comprises bismuth and dichloroacetate coordinated to the bismuth.

DETAILED DESCRIPTION

Figure 1:
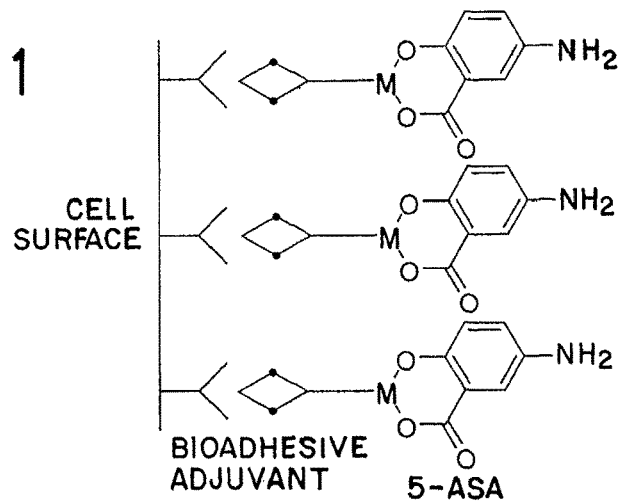
FIG. 1 shows a schematic illustration of monomeric bioadhesive adjuvants coordinated to monomeric metal-containing compounds.

As further described below, the inventors have discovered that coordinating a metal to a biologically active agent—particularly though not exclusively to a biologically active agent intended for peroral administration—enables modulation of the biologically active agent's pharmacokinetic (PK) properties and results in a compound that exhibits improved pharmacokinetic properties relative to the uncoordinated biologically active agent. In some embodiments, an adjuvant is also coordinated to the metal, which results in a compound that exhibits improvements in PK properties relative to uncoordinated biologically active agent. The inventors have further discovered that coordination to a metal—particularly though not exclusively bismuth—provides an effective method to modulate and enhance the plasma level-time curves of levodopa, triiodothyronine, mesalamine, and dichloroacetate. In addition, it has been discovered that coordinating a biologically active agent to bismuth can provide a compound that behaves as a type of alimentary tract depot for the gradual release of a drug from a patient's gastrointestinal (GI) tract.

Throughout this description and in the appended claims, the following definitions are to be understood:

The phrase "coordinated to" and the term "coordination" as used in relation to "bismuth-containing compounds" encompass a range of different types of bonding forces that can exist between a bismuth atom or ion and a heteroatom-containing ligand. These bonding forces include but are not limited to coordinate covalent bonding, ionic bonding, chelation, ion pairing, and the like, and combinations thereof.

The phrase "bismuth-containing compound" as used herein refers to monomeric as well as oligomeric and polymeric structures. In view of a well-known proclivity of bismuth complexes to cross-link and/or polymerize, it is to be understood that references herein to "bismuth-containing compounds" encompass discrete monomeric complexes as well as two-dimensional sheet-like structures and/or three-dimensional structures. In addition, in view of the difficulty that exists in definitively and unambiguously characterizing the nature of the bonding in such compounds, the phrase "bismuth-containing compound" is intended as a generic description that encompasses and is used interchangeably with phrases like "bismuth complex," bismuth coordination complex," "bismuth salt," and the like.

The phrase "biologically active agent" refers generally and without limitation to any compound that triggers—either directly or indirectly—a physiological response in a patient, desirably though not necessarily a therapeutically efficacious response. As used herein, the phrase "biologically active agent" is used interchangeably with the phrase "pharmaceutical agent" and the term "drug."

The phrase "coordination polymer" refers to an assembly of one-, two- or three-dimensional networks centered around a metal atom, ion or cluster.

By way of general introduction, a metal-containing compound in accordance with the present teachings includes a first metal and a biologically active agent coordinated to the first metal. In some embodiments, a pharmacokinetic property of the metal-containing compound is modulated relative to the corresponding pharmacokinetic property of the biologically active agent in an uncoordinated state. In some embodiments, the metal-containing compound further includes a second metal. In some embodiments, the second metal is also coordinated to the biologically active agent. In some embodiments, the first metal and the second metal are different.

In some embodiments, the first metal and the second metal are independently selected from group IIA metals, p-block metals, transition metals, lanthanides, and actinides. In some embodiments, the first metal and/or the second metal is a p-block metal. In some embodiments, the first metal and the second metal are each independently selected from group IIIA metals, group IVA metals, and group VA metals. In some embodiments, the first metal and/or the second metal is each independently a group VA metal. In some embodiments, the first metal and/or the second metal are each independently bismuth.

A bismuth-containing compound in accordance with the present teachings includes bismuth and a biologically active agent coordinated to the bismuth. In some embodiments, a pharmacokinetic property of the bismuth-containing compound is modulated relative to the corresponding pharmacokinetic property of the biologically active agent in an uncoordinated state. In some embodiments, the bismuth containing-compound further comprises a second metal. In some embodiments, the second metal is also coordinated to the biologically active agent. In some embodiments, the second metal is different than bismuth.

All manner of biologically active agents capable of coordinating with a metal (e.g., bismuth, etc.) to form a stable compound are contemplated for use in accordance with the present teachings—particularly though not exclusively drugs that need to be maintained above a minimum effective clinical plasma level over a longer therapeutic window than can otherwise be achieved via a single immediate release (IR) dosage. Representative agents contemplated for use include but are not limited to the following: medicaments for treating the gastrointestinal (GI) tract (e.g., antacids; reflux suppressants; antiflatulents; antidopaminergics; proton pump inhibitors (PPIs); H$_2$-receptor antagonists; cytoprotectants; prostaglandin analogues; laxatives; antispasmodics; antidiarrheals; bile acid sequestrants; opioids; and the like); medicaments for treating the cardiovascular system (e.g., β-receptor blockers; calcium channel blockers; diuretics; cardiac glycosides; antiarrhythmics; nitrate; antianginals; vasoconstrictors; vasodilators; peripheral activators; and the like); antihypertension agents (e.g., ACE inhibitors; angiotensin receptor blockers; a blockers; and the like);

coagulation agents (e.g., anticoagulants; heparin; antiplatelet drugs; fibrinolytics; anti-hemophilic factors; haemostatic drugs; and the like); atherosclerosis/cholesterol inhibitors (e.g., hypolipidaemic agents; statins; and the like); medicaments that affect the central nervous system (e.g., hypnotics; anesthetics; antipsychotics; antidepressants including but not limited to tricyclic antidepressants, monoamine oxidase inhibitors, selective serotonin reuptake inhibitors, etc.; and the like); antiemetics; anticonvulsants; antiepileptics; anxiolytics; barbiturates; movement disorder drugs including but not limited to those for treating Parkinson's disease, etc.; stimulants including but not limited to amphetamines; benzodiazepines; cyclopyrrolones; dopamine antagonists; antihistamines; cholinergics; anticholinergics; emetics; cannabinoids; 5-HT serotonin antagonists; and the like); analgesics (e.g., non-steroidal anti-inflammatory drugs or NSAIDs; opioids; various orphan drugs including but not limited to paracetamol, tricyclic antidepressants, anticonvulsants, etc.; and the like); medicaments for treating musculoskeletal disorders (e.g., NSAIDs including but not limited to COX-2 selective inhibitors, etc.; muscle relaxants; neuromuscular drugs; anticholinesterases; and the like); medicaments for treating the eye (e.g., adrenergic neurone blockers; astringents; ocular lubricants; mydriatics; cycloplegics; anti-glaucoma agents including but not limited to adrenergic agonists, β-blockers, carbonic anhydrase inhibitors/hyperosmotics, cholinergics, miotics, parasympathomimetics, prostaglandin agonists/prostaglandin inhibitors, nitroglycerin, etc.; and the like); topical anesthetics (e.g., benzocaine; butamben; dibucaine; lidocaine; oxybuprocaine; pramoxine; proparacaine; proxymetacaine; tetracaine; and the like); sympathomimetics; parasympatholytics; anti-bacterial agents (e.g., antibiotics; topical antibiotics; sulfa drugs; aminoglycosides; fluoroquinolones; and the like); antiviral drugs; medicaments for treatment of the ear, nose, and throat (e.g., sympathomimetics; antihistamines; anticholinergics; NSAIDs; steroids; antiseptics; local anesthetics; antifungals; cerumenolyti; and the like); medicaments for treating the respiratory system (e.g., bronchodilators; NSAIDs; anti-allergics; antitussives; mucolytics; decongestants; corticosteroids; β-2-adrenergic agonists; anticholinergics; steroids; and the like); medicaments for treating diseases of the endocrine system (e.g., androgens; antiandrogens; gonadotropin; corticosteroids; human growth hormone; insulin; antidiabetics including but not limited to sulfonylureas, biguanides/metformin, thiazolidinediones, insulin, etc.; thyroid hormones; antithyroid drugs; calcitonin; diphosphonate; vasopressin analogues; and the like); medicaments for treating the reproductive system and urinary system (e.g., antifungals; alkalizing agents; quinolones; antibiotics; cholinergics; anticholinergics; anticholinesterases; antispasmodics; 5-α reductase inhibitor; selective α-1 blockers; sildenafils; fertility medications; and the like); contraceptives (e.g., hormonal contraceptives; and the like); medicaments for use in obstetrics and gynecology (e.g., NSAIDs; anticholinergics; haemostatic drugs; antifibrinolytics; hormone replacement therapy (HRT); bone regulators; β-receptor agonists; follicle stimulating hormone; luteinizing hormone; luteinizing-hormone-releasing hormone (LHRH); gonadotropin release inhibitor; progestogen; dopamine agonists; oestrogen; prostaglandins; gonadorelin; diethylstilbestrol; and the like); medicaments for treating the skin (e.g., emollients; anti-pruritics; antifungals; disinfectants; scabicides; pediculicides; tar products; vitamin A derivatives; vitamin D analogues; keratolytics; abrasives; systemic antibiotics; topical antibiotics; hormones; desloughing agents; exudate absorbents; fibrinolytics; proteolytics; sunscreens; antiperspirants; corticosteroids; and the like); medicaments for treating infections and infestations (e.g., antibiotics; antifungals including but not limited to imidazoles, polyenes, etc.; antileprotics; antituberculous drugs; antimalarials; anthelmintics; amoebicides; antivirals; antiprotozoals; antiparasitics; and the like); anti-inflammatory agents (e.g., NSAIDs; corticosteroids; and the like); medicaments for treating the immune system (e.g., vaccines; immunoglobulins; immunosuppressants; interferons; monoclonal antibodies; and the like); medicaments for treating allergies (e.g., anti-allergics; antihistamines; NSAIDs; mast cell inhibitors; and the like); nutritional agents (e.g., tonics; iron preparations; electrolytes; parenteral nutritional supplements; vitamins; anti-obesity drugs; anabolic drugs; haematopoietic drugs; food product drugs; and the like); antineoplastic agents (e.g., cytotoxic drugs; therapeutic antibodies; sex hormones; aromatase inhibitors; somatostatin inhibitors; recombinant interleukins; G-CSF; erythropoietin; and the like); euthanaticum agents; and the like; and combinations thereof.

In some embodiments, representative biologically active agents contemplated for use in accordance with the present teachings include but are not limited to the following: anti-infectives (e.g., amoebicides; aminoglycosides; anthelmintics; antifungals including but not limited to azole antifungals, echinocandins, polyenes, etc.; antimalarial agents including but not limited to antimalarial combinations, antimalarial quinolines, etc.; antituberculosis agents including but not limited to aminosalicylates, antituberculosis combinations, nicotinic acid derivatives, rifamycin derivatives, *streptomyces* derivatives, etc.; antiviral agents including but not limited to adamantane antivirals, antiviral combinations, antiviral interferons, chemokine receptor antagonists, integrase strand transfer inhibitors, neuraminidase inhibitors, non-nucleoside reverse transcriptase inhibitors or NNRTIs, nucleoside reverse transcriptase inhibitors or NRTIs, protease inhibitors, purine nucleosides, etc.; carbapenems; cephalosporins including but not limited to first generation cephalosporins, second generation cephalosporins, third generation cephalosporins, fourth generation cephalosporins, next generation cephalosporins, etc.; glycopeptide antibiotics; glycylcyclines; leprostatics; lincomycin derivatives; lipoglycopeptides; macrolide derivatives including but not limited to ketolides, macrolides, etc.; antibiotics; penicillins including but not limited to aminopenicillins, antipseudomonal penicillins, β-lactamase inhibitors, natural penicillins, penicillinase resistant penicillins, etc.; quinolones; sulfonamides; tetracyclines; urinary anti-infectives; and the like); anticholinergics/antispasmodics; antidiabetic agents (e.g., α-glucosidase inhibitors; antidiabetic combinations; dipeptidyl peptidase 4 inhibitors; meglitinides; non-sulfonylureas; sulfonylureas; thiazolidinediones; and the like); antigout agents; antihyperlipidemic agents (e.g., antihyperlipidemic combinations; bile acid sequestrants; cholesterol absorption inhibitors; fibric acid derivatives; statins; and the like); antihyperuricemic agents; antineoplastics (e.g., alkylating agents; anti-CTLA-4 monoclonal antibodies; antibiotics/antineoplastics; antimetabolites; antineoplastic detoxifying agents; antineoplastic interferons; antineoplastic monoclonal antibodies; BCR-ABL tyrosine kinase inhibitors; CD20 monoclonal antibodies; CD33 monoclonal antibodies; CD52 monoclonal antibodies; EGFR inhibitors; HER2 inhibitors; histone deacetylase inhibitors; hormones/antineoplastics; miscellaneous antineoplastics; mitotic inhibitors; mTOR inhibitors; mTOR kinase inhibitors; multikinase inhibitors; trifunctional monoclonal antibodies; tyrosine kinase inhibitors; VEGF/VEGFR inhibitors; and the like); cardiovascular agents (e.g., agents for hypertensive emergencies; agents for pulmonary hypertension; aldosterone receptor antagonists; angiotensin converting enzyme inhibitors; angiotensin II inhibitors; centrally acting antiadrenergic agents; peripherally acting antiadrenergic agents; α-adrenoreceptor antagonists; antianginal agents including but not limited to nitrates, etc.; antiarrhythmic agents including but not limited to group I antiarrhythmics, group II antiarrhythmics, group III antiarrhythmics, group IV antiarrhythmics, group V antiarrhythmics, etc.; anticholinergic chronotropic agents; antihypertensive combinations; β-adrenergic blocking agents including but not limited to cardioselective β blockers, non-cardioselective β blockers, etc.; calcium channel blocking agents; diuretics including but not limited to carbonic anhydrase inhibitors, loop diuretics, potassium-sparing diuretics, thiazide diuretics, etc.; inotropic agents; peripheral vasodilators; prostaglandin D2 antagonists; renin inhibitors; sclerosing agents; vasodilators; vasopressin antagonists; vasopressors; and the like); central nervous system agents (e.g., analgesics including but not limited to analgesic combinations, antimigraine agents, cox-2 inhibitors, narcotic analgesic combinations, narcotic analgesics, non-steroidal anti-inflammatory agents, salicylates, etc.; anorexiants; anticonvulsants including but not limited to barbiturate anticonvulsants, benzodiazepine anticonvulsants, carbamate anticonvulsants, carbonic anhydrase inhibitor anticonvulsants, dibenzazepine anticonvulsants, fatty acid derivative anticonvulsants, γ-aminobutyric acid analogs, γ-aminobutyric acid reuptake inhibitors, γ-aminobutyric acid transaminase inhibitors, hydantoin anticonvulsants, oxazolidinedione anticonvulsants, pyrrolidine anticonvulsants, succinimide anticonvulsants, triazine anticonvulsants, urea anticonvulsants, etc.; antiemetic/antivertigo agents including but not limited to 5HT3 receptor antagonists, anticholinergic antiemetics, phenothiazine antiemetics, etc.; antiparkinson agents including but not limited to anticholinergic antiparkinson agents, dopaminergic antiparkinsonism agents, etc.; anxiolytics, sedatives, and hypnotics including but not limited to barbiturates, benzodiazepines, etc.; cholinergic agonists; cholinesterase inhibitors; CNS stimulants; drugs used in alcohol dependence; muscle relaxants including but not limited to neuromuscular blocking agents, skeletal muscle relaxant combinations, skeletal muscle relaxants, etc.; and the like); coagulation modifiers (e.g., anticoagulants including but not limited to coumarins and indandiones, factor Xa inhibitors, heparins, thrombin inhibitors, etc.; antiplatelet agents including but not limited to glycoprotein platelet inhibitors, platelet aggregation inhibitors, etc.; platelet-stimulating agents; thrombolytics; and the like); gastrointestinal agents (e.g., 5-aminosalicylates; antidiarrheals; functional bowel disorder agents including but not limited to chloride channel activators, peripheral opioid receptor antagonists, serotoninergic neuroenteric modulators, etc.; gallstone solubilizing agents; GI stimulants; H.pylori eradication agents; H2 antagonists; proton pump inhibitors; and the like); thyroid drugs; immune globulins; immunologic agents; immunosuppressive agents; metabolic agents (e.g., bone resorption inhibitors; peripherally acting antiobesity agents; and the like); antidotes; antipsoriatics; antirheumatics; chelating agents; cholinergic muscle stimulants; genitourinary tract agents (e.g., impotence agents; tocolytic agents; urinary antispasmodics; urinary pH modifiers; uterotonic agents; and the like); antipsychotic agents; nasal antihistamines and decongestants; nasal steroids; psychotherapeutic agents (e.g., antidepressants including but not limited to monoamine oxidase inhibitors, phenylpiperazine antidepressants, selective serotonin reuptake inhibitors, serotonin-norepinephrine reuptake inhibitors, tetracyclic antidepressants, tricyclic antidepressants, etc.; antipsychotics including but not limited to atypical antipsychotics, phenothiazine antipsychotics, thioxanthenes, etc.; norepinephrine reuptake inhibitors; norepinephrine-dopamine reuptake inhibitors; psychotherapeutic combinations; and the like); respiratory agents (e.g., antiasthmatic combinations; antihistamines; antitussives; bronchodilators including but not limited to adrenergic bronchodilators, anticholinergic bronchodilators, bronchodilator combinations, methylxanthines, etc.; decongestants; expectorants; leukotriene modifiers; upper respiratory combinations; and the like); spermicides; topical agents (e.g., anorectal preparations; antiseptics and germicides; dermatological agents including but not limited to topical acne agents, topical anesthetics, topical anti-infectives, topical antibiotics, topical antifungals, topical antihistamines, topical antipsoriatics, topical antivirals, topical astringents, topical debriding agents, topical depigmenting agents, topical emollients, topical keratolytics, topical steroids, topical steroids with anti-infectives, etc.; mouth and throat products; nasal preparations including but not limited to nasal anti-infectives, etc.; otic preparations including but not limited to cerumenolytics, otic anesthetics, otic anti-infectives, otic steroids, otic steroids with anti-infectives, etc.; vaginal preparations including but not limited to vaginal anti-infectives, etc.; and the like); and the like; and combinations thereof.

In some embodiments, the biologically active agent for use in forming bismuth-containing compounds in accordance with the present teachings contains a heteroatom (e.g., oxygen, nitrogen, sulfur or selenium). In some embodiments, the biologically active agent contains an additional heteroatom in close proximity to the first heteroatom, which can participate in the bonding or otherwise chelate with bismuth to form a coordination compound. Biologically active agents having this arrangement of functional groups are well configured for bonding with bismuth, and the resultant compound containing bismuth and the biologically active agent will be stable enough in a biological system to modify the hydrolysis therein, such that the performance of the biologically active agent will be sufficiently modulated. Such hydrolytic stability imparted by multidentate ligands is supported by a lowering in $pK_a$ of the ligand, such that even amides can be deprotonated with weak bases (e.g., triethylamine) in the presence of coordinating metals. Therefore, biologically active agents with protonated heteroatoms, which normally would not be ionized under typical biological pH, can have the proton replaced by a covalently coordinated metal, thereby enhancing covalency by the additional chelation from participating heteroatoms.

In some embodiments, at least one of the heteroatoms on the biologically active agent that will bind to bismuth is oxygen, nitrogen, sulfur or selenium. In some embodiments, the biologically active agent for use in complexing with a metal other than bismuth contains a proton on a heteroatom (e.g., oxygen, nitrogen, sulfur or selenium) with a $pK_a$ slightly greater or lower than water and an additional heteroatom in close proximity to the first protonated heteroatom such that it can participate in the bonding with or otherwise chelate to the metal.

In some embodiments, the metal-containing compound comprises bismuth and a biologically active agent with at least one heteroatom configured for coordination with the bismuth. In some embodiments, the heteroatom is part of a functional group attached to a biologically active agent. Representative functional groups include but are not limited to cyclic and acyclic forms of amines, amides, alkoxides, carbamates, hydroxamates, thiocarbamates, ureides, dithiocarbamates, enolates, carboxylates, amino carboxylates, amino alkoxides, diols, hydroxyl carboxylates, sulfinates, sulfonates, thiolates, mercaptocarboxylates, thienolates, dithiocarboxylates, dithiocarbamates, dithiocarbonates, dithiophosphinates, dithiophosphates, and the like, and combinations thereof. In some embodiments, representative functional groups include but are not limited to tropolonates, benzenethiolates, benzenesulfinates, pyridine carboxylates, catecholates, and the like and combinations thereof.

In some embodiments, the heteroatom configured for coordination with bismuth is oxygen, sulfur, selenium or nitrogen. In some embodiments, the heteroatom is oxygen and the functional group providing the oxygen is a carboxyl group or a catechol hydroxy group. Representative biologically active agents containing a catechol group or diol group that are contemplated for use in accordance with the present teachings include but are not limited to rifaximin, apomorphine, epinephrine, entacapone, benserazide, tolcapone, masoprocol, quercetin, caffeic acid, isoprenaline, and combinations thereof. In some embodiments, the functional group is a carboxyl group. Representative biologically active agents containing a carboxyl group that are contemplated for use in accordance with the present teachings include but are not limited to prostaglandin $E_2$, prostaglandin $E_1$, nileprost, captopril, mycophenolic acid (mycophenolate), tranexamic acid, enalprilic acid, valproic acid, γ-hydroxybutyric acid (GHB), baclofen, 5-aminosalicylic acid, methyldopa, levodopa, tranexamic acid, furosemide, methotrexate, chlorambucil, 6-aminocaproic acid, tretinoin, D,L-2,4-dihydroxyphenylalanine, ethacrynic acid, penicillamine, probenicid, carbidopa, melphalan, fusidic acid, L-cysteine, 7-theophylline acetic acid, nicotinic acid, L-thyroxine, bumetanide, folic acid, retinoic acid, isonipecotic acid, glutathione, acivicin, loflazepate, iopanoic acid, phenylalanylalanine, cysteamine, N-acetylcysteine, ticrynafen, folinic acid, orotic acid, biotin, oleic acid, linoleic acid, cholic acid, salazosulfapyridine, azodisal, etretinic acid, and combinations thereof. In some embodiments, the biologically active agent is selected from the group consisting of triiodothyronine, levodopa, dichloroacetate, mesalamine, and combinations thereof. In some embodiments, the biologically active agent is levodopa.

In some embodiments, the biologically active agent and the metal—which, in some embodiments, is bismuth—are coordinated through a single point of attachment, whereas in other embodiments, the biologically active agent and the metal are coordinated through multiple points of attachment (e.g., a polydentate ligand).

In some embodiments, the metal-containing compound—which, in some embodiments, is a bismuth-containing compound—further includes an adjuvant coordinated to the metal. In some embodiments, the adjuvant is selected from the group consisting of lipids, carbohydrates, amino acids, bioadhesive polymers, peptides, bile acids, and combinations thereof. In some embodiments, the adjuvant is a carbohydrate. In some embodiments, the adjuvant is selected from the group consisting of ascorbic acid, citric acid, arginine, glycine, leucine, carnosine, ferulic acid, alginic acid, sodium alginate, chitosan, chitin, polyacrylic acids, pectin, pullulan, hydroxypropylmethylcellulose, and combinations thereof.

By way of further general introduction, a coordination polymer in accordance with the present teachings includes a polymer matrix that contains a metal-containing compound. In some embodiments, the metal-containing compound is a bismuth-containing compound that includes bismuth and a biologically active agent coordinated to the bismuth. In some embodiments, the biologically active agent includes at least one heteroatom configured for coordination with the metal, and is selected from the group consisting of triiodothyronine, levodopa, dichloroacetate, mesalamine, and combinations thereof. In some embodiments, the polymer matrix includes an alginic acid hydrogel.

By way of further general introduction, a method for modulating a pharmacokinetic property of a biologically active agent in accordance with the present teachings includes coordinating the biologically active agent to a metal to form a metal-containing compound, and administering the metal-containing compound orally to a patient. In some embodiments, a pharmacokinetic property of the biologically-active agent released from the metal-containing compound is modulated relative to the biologically active agent in an uncoordinated state. In some embodiments, the metal-containing compound is a bismuth-containing compound.

In some embodiments, the pharmacokinetic property that is modulated is selected from the group consisting of release duration, peak plasma concentration, absorption, bioavailability, variability of absorption, toxicity, and combinations thereof. In some embodiments, the biologically active agent released from the metal-containing compound—which, in some embodiments, is a bismuth-containing compound—exhibits an enhancement in one or more of release duration, peak plasma concentration, absorption, and bioavailability relative to biologically active agent in an uncoordinated state. In some embodiments, the biologically active agent released from the metal-containing compound—which, in some embodiments, is a bismuth-containing compound—exhibits a reduction in one or more of peak plasma concentration, absorption, variability of absorption, and toxicity. In some embodiments, the metal-containing compound—which, in some embodiments, is a bismuth-containing compound—exhibits enhanced bioadhesion relative to the biologically active agent in an uncoordinated state.

In some embodiments, the biologically active agent is selected from the group consisting of levodopa, triiodothyronine, mesalamine, dichloroacetate, and combinations thereof. In some embodiments, the metal-containing compound—which, in some embodiments, is a bismuth-containing compound—further comprises an adjuvant coordinated to the metal.

In some embodiments, the method for modulating a pharmacokinetic property of a biologically active agent further includes co-administering to the patient a pharmaceutical agent that acts to enhance a pharmacokinetic property of the metal-containing compound. In some embodiments, the metal-containing compound is a bismuth-containing compound.

As further explained below, bismuth compounds in general have a tendency to reside in the GI tract. As such, bismuth-containing compounds in accordance with the present teachings can be designed to behave as alimentary tract depots for the gradual release of a drug. Accordingly, in some embodiments, the biologically active agent is transported to a desired site in the patient's alimentary tract and released into the patient primarily from the desired site. In some embodiments, the desired site is selected from the group consisting of the patient's stomach, duodenum, jejunum, ileum, colon and combinations thereof.

By way of further general introduction, a method for treating PD includes administering a metal-containing compound orally to a patient. In some embodiments, the metal-containing compound is a bismuth-containing compound and includes bismuth and LD coordinated to the bismuth. In some embodiments, the bismuth-containing compound further comprises an adjuvant which, in some embodiments, is selected from the group consisting of carbohydrates, amino acids, lipids, bioadhesive polymers, peptides, bile acids, and combinations thereof. In some embodiments, the carbohydrates comprise ascorbic acid; the amino acids are selected from the group consisting of arginine, glycine, leucine, and combinations thereof; the lipids comprise ferulic acid; the bioadhesive polymers are selected from the group consisting of alginic acid, sodium alginate, chitosan, chitin, polyacrylic acids, pectin, pullulan, hydroxypropylmethylcellulose, and combinations thereof; and the peptides comprise carnosine.

In some embodiments, the method for treating PD further comprises co-administering to the patient a pharmaceutical agent that inhibits extracerebral decarboxylation of the LD. Representative agents for co-administration include but are not limited to carbidopa, benserazide, entacapone, and combinations thereof. In some embodiments, the pharmaceutical agent is provided as an adjuvant that, like LD, is coordinated to the metal.

By way of further general introduction, a method for treating hypothyroidism includes administering a metal-containing compound orally to a patient. In some embodiments, the metal-containing compound is a bismuth-containing compound and comprises bismuth and 3,5,3'-triiodothyronine (a.k.a., triiodothyronine, liothyronine or T3) coordinated to the bismuth. In some embodiments, the method further includes co-administering thyroxine (T4) to the patient.

By way of further general introduction, a method for treating ulcerative colitis includes administering a metal-containing compound orally and/or rectally to a patient. In some embodiments, the metal-containing compound is a bismuth-containing compound and comprises bismuth and mesalamine coordinated to the bismuth.

In some embodiments, the metal-containing compound—which, in some embodiments, is a bismuth-containing compound—further comprises an adjuvant. In some embodiments, the adjuvant is an intercellular adhesion molecule (ICAM) binder. In other embodiments, the adjuvant is a bioadhesive agent with representative agents including but not limited to glucosamine, mannuronic acid, and a combination thereof. In some embodiments, the bioadhesive agent has a monomeric structure while the metal-containing compound has either a monomeric or polymeric structure. In other embodiments, the bioadhesive agent has a polymeric structure while the metal-containing compound has a monomeric structure.

Finally, by way of general introduction, a method for treating cancer includes administering a metal-containing compound orally to a patient. In some embodiments, the metal-containing compound is a bismuth-containing compound and comprises bismuth and dichloroacetate coordinated to the bismuth. In some embodiments, a degree of peripheral neuropathy induced by the dichloroacetate released from the bismuth-containing compound is less than a degree of peripheral neuropathy induced by dichloroacetate in an uncoordinated state.

The present inventors have investigated the preparation of coordination compounds formed between metals and drug ligands. Coordination compounds (a.k.a. metal complexes or chelates) contain a metal atom or ion and one or more ligands (e.g., atoms, ions, or molecules) that formally donate electrons to the metal. Traditionally, a chelation compound refers to a combination of a metallic ion bonded to one or more chelating ligands. A chelating ligand (or chelate) is a polydentate ligand configured for having two or more points of attachment to the metal ion (e.g., forming a heterocyclic ring structure). Thus, chelation compounds are traditionally regarded as a sub-set of coordination compounds.

Without wishing to be bound by a particular theory or to in any way limit the scope of the appended claims or their equivalents, it is presently believed that in these coordination complexes, the drug ligand at least partially neutralizes the positive charge of the metal ion through the formation of a combination of ionic and coordinate covalent bonds—as opposed to the purely electrostatic attraction observed in salts. While electrostatic attraction can also exist in coordination complexes, the complexes additionally have an inherently covalent coordination bond between the metal and drug ligand. It is presently believed that this enhanced covalency of the coordination complex is primarily responsible for reducing the $pK_a$ of its acidic protons, such that solutions of these coordination compounds are stable at physiological pH, as well as for modulating the pharmacokinetic properties of the drug ligand relative to its uncoordinated state.

In accordance with the present teachings, it has been discovered that under certain conditions and/or with certain metals, insoluble crystal structures can be produced. The insoluble nature of such metal:drug complexes provides a means to slowly deliver a drug to a target organ as the metal:drug bond is hydrolyzed in the alimentary tract or systemically. The metal:drug complex can be delivered to a target organ using drug delivery formulations previously developed for this purpose. Moreover, due to the multiplicity of binding sites imparted by polymeric materials, polymer crystal structures can exhibit very strong bioadhesive properties. In addition, polymeric structures can form biofilms on mucosal surfaces, thereby enhancing their bioadhesive properties. Thus, in some embodiments in accordance with the present teachings, the metal:drug complex has a polymeric structure. In some embodiments, polymeric adjuvants can be used to transfer the polymer properties to a metal:drug complex.

Alginic acid has been used as a biopolymer to control the release of drugs, whereby dried alginate beads can re-swell upon exposure to biological fluids. The swelled beads, or hydrogels, create a diffusion barrier for encapsulated compounds, such as drugs, which can slow the migration of the drug out of the hydrogel. Metal-containing salts (e.g., calcium salts) in the alginate coating further slows release. This observation supports a premise in accordance with the present teachings that coordinating a drug with a metal inside an alginate hydrogel will have a significant impact on the plasma level-time curve of the drug. Thus, in some embodiments, release of the drug from the polymer matrix is slowed by virtue of the metal binding the drug to the bioadhesive polymer. The kinetics of breaking the metal:polymer bond can be more tightly controlled than the kinetics of breaking the various drug:polymer hydrogen bonds and lipophilic interactions. Thus, in some embodiments, metal coordination facilitates the formation of a bond between a bioadhesive polymer and a drug.

In some embodiments, the metal used for coordination with a drug ligand is bismuth. It has been discovered that a single point of attachment between bismuth and a heteroatom on the drug ligand is sufficient to form a complex stable enough to impart modulated pharmacokinetics. Chelation with polydentate ligands is also an acceptable bonding mode for bismuth-containing compounds in accordance with the present teachings and may provide added benefit although it is not necessary. In some embodiments, the bond between a drug ligand and a bismuth atom has a single point of attachment, whereas in other embodiments, the bond has multiple points of attachment. Without wishing to be bound by a particular theory or to in any way limit the scope of the appended claims or their equivalents, it is presently believed that the ability to bond through a single point of attachment is likely due to the polymeric nature that exists between organic ligands bound to bismuth.

Bismuth has a history of safe use in oral medications. Bismuth-containing over-the-counter (OTC) products have been used for over 100 years to ameliorate stomach upset (e.g., the bismuth subsalicylate formulation sold under the tradename PEPTO-BISMOL by Procter & Gamble). In addition, bismuth-containing drugs have been approved by the FDA for eradicating *H.pylori*-induced ulcers.

Without wishing to be bound by a particular theory or to in any way limit the scope of the appended claims or their equivalents, it is presently believed that bismuth's gastroadhesive properties at least in part result from the precipitation of bismuth compounds in the GI tract to form extremely insoluble and poorly absorbed complexes.

In one study, a group of researchers demonstrated that the salicylate portion of PEPTO-BISMOL is largely absorbed over a 6-hour time period whereas the absorption of bismuth over the same time period was negligible. Salicylate appeared in the blood 30 minutes after dosing (with 90% ultimately being absorbed), whereas bismuth shows up only in very small amounts several hours after dosing and has been shown to persist in the body for at least 3 months following a 6-week course of treatment of the drug.

It has also been demonstrated that bismuth has a tendency to adhere to the intestinal tracts of dogs. For example, twelve weeks after dogs were fed with large doses of bismuth carbonate, the largest amount of bismuth was still found in the intestine. These observations support a premise in accordance with the present teachings that bismuth complexes can be provided to behave as alimentary tract depots for the gradual release of a drug.

Without wishing to be bound by a particular theory or to in any way limit the scope of the appended claims or their equivalents, it is presently believed that a polymeric crystal structure of organo-bismuth compounds may additionally—or alternatively—be responsible for the gastric retentive properties of bismuth-containing compounds. Bismuth complexes typically form complicated polymeric structures marked by cross-linking from different directions forming a two-dimensional sheet and three-dimensional structures into a large mesh with channels. These unique sheet-like polymeric structures may be responsible for the antiulcer activity of the complexes (e.g., by selectively depositing on the ulcerous craters to form a protective coating). Tiny crystals and a unique bismuth coating have been observed in ulcer craters in animal models and patients following administration of colloidal bismuth subcitrate.

In a first series of embodiments, the biologically active agent coordinated to a metal is LD. By way of introduction, treatment for the motor dysfunction associated with PD typically involves agents that are converted to dopamine, possess dopaminergic activity or increase dopamine availability within the central nervous system (CNS). Dopamine replacement therapy is classically accomplished by the oral administration of LD—a metabolic precursor of dopamine—for transport across the blood brain barrier (BBB) where decarboxylation can occur. In order to inhibit peripheral decarboxylation, other drugs (e.g., carbidopa and benserazide) can be administered simultaneously. More recently, a third drug—entacapone, which inhibits LD metabolism by catechol-O-methyltransfersase (COMT)—has been used to improve LD's short plasma half-life (e.g., the combination of carbidopa, LD, and entacapone sold under the tradename STALEVO by Novartis Pharmaceuticals).

LD remains the most effective drug for the symptomatic control of PD and for improving the quality of life for patients. Originally administered as an IV infusion in 1960, it was 7 years before a published account appeared describing the successful oral administration of LD. Many refinements in the use of 3,4-dihydroxyphenylalanine (DOPA) have been made through the years in order to improve potency and duration and minimize adverse effects (e.g., nausea). These refinements include eliminating the dextroisomer from the racemate, formulating sustained-release dosage forms, and concurrently administering enzyme inhibitors to decrease DOPA metabolism. Notwithstanding, LD therapy remains in need of further refinement, as further explained below.

Extensive efforts have been made to replace LD with direct acting dopamine receptor agonists, which offer better absorption properties and longer half-lives relative to LD. Progress has been made in developing dopamine agonists with a variety of affinity values for a variety of dopamine receptor subtypes. However, while these drugs (e.g., pramipexole, ropinirole, and carbergoline) have proved to be valuable adjuncts to LD and can even substitute—at least initially—for LD, they cannot permanently replace it. Whether due to dopamine's unique activity and/or the neurotransmitter activity of LD itself, this tried and true "gold standard" provides uniquely effective therapy. A variety of prodrugs have also been studied but none has been marketed to date. In addition, other drugs have been used as adjuncts to LD (e.g., cholinergic antagonists, NMDA antagonists, and adenosine $A_{2A}$ receptor antagonists), and alternative routes of administration (e.g., methyl ester of LD patch) have been explored.

Maintaining consistent carbidopa-LD plasma levels presents a significant challenge in the treatment of PD due to variable absorption, gastrointestinal symptoms, and/or patient compliance issues. Moreover, factors such as gender, age, and gastric motility may affect the bioavailability of LD due to its low water and lipid solubility. After several years of treatment, a gradual decline in responsiveness to LD generally occurs, which requires patients to increase the dosage and frequency of administration in order to achieve the same effectiveness against the bradykinesia, rigidity, and tremors characteristic of PD (i.e., the "wearing-off effect"). Moreover, LD therapy also has CNS side effects and new motor complications including dyskinesia, dystonia, the "on-off effect," and end-of-dose deterioration, which are further exacerbated by increases in LD dosing.

In addition to the above, the fast and extensive metabolism of LD further complicates dosing parameters. Thus, the co-administration of a peripheral decarboxylase inhibitor (e.g., carbidopa) with LD to minimize its conversion to dopamine prior to entering the brain is standard practice, and serves to increase brain LD levels while also minimizing the nausea and vomiting induced by peripheral dopamine. The use of monoamine oxidase type B (MAO-B) inhibitors (e.g., selegiline, rasagiline) extends the activity of dopamine by blocking its oxidative deamination to dihydroxyphenylacetic acid (DOPAC). In addition, as described above, inhibitors of COMT such as entacapone are invoked to decrease the conversion of dopamine to 3-methoxytyramine. COMT inhibitors are also effective in minimizing the conversion of LD to 3-O-methyldopa (3-OMD), which can occur during absorption and decrease bioavailability.

Without wishing to be bound by a particular theory or to in any way limit the scope of the appended claims or their equivalents, it is presently believed that the altered availability of dopamine within the brain may also contribute to the loss in long-term effectiveness of LD. There is growing evidence to suggest that the integrity of the BBB itself is compromised as PD progresses. Whether BBB dysfunction is due to cellular death, chronic inflammation, reduced expression of P-glycoproteins, neovascularization and/or other mechanisms is not clearly understood at this time. Additionally, dysfunction of the BBB can result in serious health issues, wherein toxins and metabolites that are normally filtered out by the BBB are allowed to pass through uninhibited. Such leakiness of the BBB is believed to possibly allow decarboxylase inhibitors such as carbidopa to enter the brain, thereby preventing the conversion of LD to dopamine.

The idea that LD may be toxic to dopaminergic neurons has been considered based on in vitro studies. However, these lines of evidence were not observed in vivo where other compensatory factors might be at work. Notwithstanding, the complications of long-term use seem to arise as a result of changes to dopaminergic neurons and/or receptors related to the progression of PD. As time passes, the therapeutic window of LD clinical efficacy tends to narrow significantly as patients progress from early to moderate and advanced stages of PD. At the same time, the duration of effect becomes shorter until it effectively mirrors LD plasma levels. As a result of these complications, achieving target plasma levels or maintaining a consistent dopaminergic effect from orally administered LD remains ones of the biggest challenges in the treatment of PD.

Emerging evidence suggests that pulsatile LD administration can play a significant role in causing the above-described complications. When first used in patients not previously exposed to the drug, a traditional dosing schedule of LD typically works extremely well in improving motor function and other symptoms of PD. At this stage, a sufficient number of basal ganglia nerve terminals exist in the striatum to store dopamine from LD, and postsynaptic receptor sensitivity is relatively normal. However, as the striatum continues to suffer progressive denervation, fewer terminals are able to store dopamine resulting in a loss of buffering capacity for exogenous LD. Changes can also occur to the dopamine receptors leading to sensitization and/or tolerance. Either way, it is very difficult to maintain LD levels high enough to avoid "off" periods but low enough to avoid dyskinesia.

When concentrations are above the dyskinesia threshold, patients experience a variety of disturbing abnormal involuntary movements that can be more bothersome than the disease symptoms. The possibility that LD itself was the cause of this narrowing window has been considered. However, without wishing to be bound by a particular theory or to in any way limit the scope of the appended claims or their equivalents, it is presently believed based on evidence that the problem is not LD but rather the way in which the drug is administered. Current thinking has focused on risks associated with the pulsatile delivery of LD in which plasma levels increase rapidly after dose administration and surpass the upper limit of the therapeutic window. Once the absorption phase has passed, rapid metabolism of LD causes an abrupt decrease in plasma levels below the response threshold. When levels are below the minimal effective concentration, patients experience "off" times. Thus, the effectiveness of LD in treating PD can be improved by altering the method and timing of drug administration.

It is possible that the problems seen with long-term LD therapy might be avoided if LD levels can be controlled so as to remain within the therapeutic window throughout all stages of treatment. Since LD is presently thought to be nontoxic, many specialists in the treatment of movement disorders prefer to start LD as early as possible. The idea of providing continuous dopaminergic stimulation (CDS) with LD to all PD patients has been gaining clinical acceptance, albeit with caveats. While STALEVO—the first product to combine carbidopa and entacapone with LD in a single dosage form—may represent an improvement, it does not eliminate fluctuations in plasma LD levels. Accordingly, in accordance with the present teachings, a goal to develop a long-acting oral formulation of LD that provides comparable anti-parkinsonian benefits without accompanying motor complications has been advanced.

Data show that the continuous release (CR) formulation is even more dependent on gastric emptying than the immediate release (IR) formulation, and the effects of slow release formulations have been disappointing. By contrast, continuous infusions of LD/carbidopa—via intravenous or intraduodenal administration—provide excellent control of LD plasma levels. These clinical effects are mirrored very well by LD plasma levels.

It was found that a continuous infusion of L-DOPA—by intravenous or intraduodenal administration—provides close to optimal pharmacokinetics. Such an infusion provides CDS and steady plasma L-DOPA levels, which lead to steadily replenished brain dopamine and constant stimulation of brain dopamine receptors. A product that delivers LD/carbidopa directly into the duodenum where absorption occurs (e.g., such as that sold under the tradename DUODOPA by Solvay Pharmaceuticals), has been well-received due to the benefits it provides to late-stage PD patients. Without wishing to be bound by a particular theory or to in any way limit the scope of the appended claims or their equivalents, it is presently believed that CDS provides both a reduction of core symptoms and drug-induced dyskinesias. However, LD infusions are not practical for most PD patients. Infusion therapies are clearly more effective but they are expensive and cumbersome and not likely to be acceptable to patients in early stages of the disease. Therefore, in accordance with the present teachings, a goal of optimizing LD pharmacokinetics with an orally administered drug product has been advanced.

Prodrugs have been developed to circumvent the above-described problem. Ideally, a prodrug should be soluble in water and in lipids, completely absorbed by the GI tract without chemical degradation or metabolism, and able to deliver parental drug into the blood stream at reproducible therapeutic levels. To date, studies have not yet translated into an FDA-approved drug product that is more effective than LD.

Delivering LD through an external pump (e.g., with DUODOPA in a depot delivery system) or increasing the residence time of LD in the GI tract are examples of methods by which CDS has been or can be optimized. In accordance with the present teachings, prolonging the residence time of drugs in the stomach and small intestine can be accomplished by formulating the drug with a bioadhesive polymer due to its ability to adhere to the stomach and/or intestinal lining.

In accordance with the present teachings, an LD compound that is slowly released from the stomach can be obtained by imparting inherent covalency and stability to a metal:LD complex using techniques of metal coordination chemistry. In further accordance with the present teachings, bioadhesive properties can be imparted to LD through coordination with a metal such that when targeted to the stomach, duodenum or jejunum, these bioadhesive properties can extend the release of LD over longer periods of time. In some embodiments, the bioadhesive mechanism of extended absorption of LD result in improved CDS. In some embodiments, the metal:LD complex is targeted to the stomach. In some embodiments, the metal is bismuth.

Continuous release LD/carbidopa formulations (e.g., SINEMET-CR) can also benefit from metal complexation in accordance with the present teachings. In such a way, the availability of LD to the brain can be increased through a combination of increased systemic bioavailability, decreased extracerebral decarboxylation, facilitated passage through the BBB, and attenuation of the pulsatile delivery typically seen with frequent administration regimens. Increased bioavailability would, in turn, dampen the required increased dosing of the product, thereby further reducing the variability of LD plasma levels.

In a second series of embodiments, the biologically active agent coordinated to a metal is liothyronine. By way of introduction, the primary function of the thyroid gland is to synthesize two hormones—thyroxine (T4) and liothyronine (3,5,3'-triiodothyronine or T3)—which play a key role in metabolic homeostasis. Once released into the bloodstream, both hormones quickly bind to transport proteins such as thyroxine-binding globulin, transthyretin and, to a much lesser extent, thyroxine-binding albumin. Ultimately, the hormones initiate transcription of genes in the nucleus of target cells with T3 believed to be 3 times more potent than the pro-hormone, T4. Thus, virtually every organ in the body is affected by the thyroid hormones.

In healthy individuals, thyroid function and particularly serum concentrations of T4 and T3 are regulated by a negative feedback system: the hypothalamic thyroid releasing hormone (TRH) stimulates the pituitary gland to produce thyroid stimulating hormone (TSH), which stimulates the thyroid gland to produce and release T4 and T3. Circulating thyroid hormones inhibit TRH and TSH, thereby down-regulating the production of T4 and T3 and completing the feedback loop. Metabolic equilibrium is maintained by this negative feedback system, such that the thyroid gland normally releases an estimated 70-90 μg of T4 and 15-30 μg of T3 into the bloodstream per day. Without wishing to be bound by a particular theory or to in any way limit the scope of the appended claims or their equivalents, it is presently believed that while T3 is secreted by healthy thyroids, the major portion of T3 in circulation is believed to result from de-iodination of T4 by peripheral tissues, such as the liver.

Hypothyroidism is the most common disorder associated with thyroid dysfunction and occurs when the amount of hormone released into the bloodstream is unable to satisfy the metabolic requirement. The clinical symptoms of hypothyroidism can include one or more of cold and exercise intolerance, decreased cardiac output, fatigue, lethargy, chronic constipation, apathy, decreased sweating, and changes in the hair and skin. Laboratory tests can reveal one or more of low sodium, low blood glucose, elevated cholesterol and triglycerides, and anemia. Mental symptoms associated with hypothyroidism can include one or more of depression, impaired memory, social withdrawal, general slowing of function, and mood disorders.

In the United States, hypothyroidism is typically caused by autoimmune destruction of the thyroid (Hashimoto's disease), $^{131}$I therapy or ablative surgery. It is estimated that 4-5 million people in the United States have been diagnosed with hypothyroidism but that there may be as many as 10 million undiagnosed people with low thyroid function. Symptoms associated with hypothyroidism are sometimes confused with aging, menopause, and stress. Sub-clinical hypothyroidism, of which an estimated 10% of older women suffer, may play a role in depression and/or mood disorders.

The conventional treatment for hypothyroidism is to simply replace the thyroid hormone no longer available from the thyroid gland. In practice, this approach is convenient since the hormone is not a peptide but a single amino acid residue (T3 or T4) and, as such, is well absorbed from the GI tract when taken orally. The first product to treat hypothyroidism was a combination of T3 and T4 derived from desiccated pig thyroid. Refined versions of this treatment regimen—such as Westhroid and Armour Thyroid are still used to a limited extent. However, since potency (i.e., micrograms of T3 and T4 per tablet) of this natural product cannot be quantified precisely, current standard practice typically involves the oral administration of T4 alone in view of the belief that T3 would be made from T4 in the de-iodination metabolic reaction described above. There are several products on the market that contain T4 including those sold under the tradenames SYNTHROID (Abbott Laboratories), LEVOTHROID (Forest Pharmaceuticals, Inc.), and LEVOXYL (King Pharmaceuticals, Inc.). T3 is also used in the treatment of hypothyroidism (e.g., CYTOMEL sold by King Pharmaceuticals), as is a combination of T4 and T3 (e.g., THYROLAR sold by Forest Pharmaceuticals, Inc.). Although neither of these T3-containing products is widely used, there is a growing understanding of the potential value of a T4/T3 combination product to treat hypothyroid states and their associated mood disorders.

The conventional wisdom of treating thyroid disorders with T4 alone has been reexamined lately. It has long been believed that T4 provides both T4 and T3 due to the body's ability to convert T4 to T3. However, not all of the T3 normally found in serum is derived from T4, with about 20% of the T3 circulating in humans being secreted directly by the normal thyroid gland. Without a functioning thyroid gland, when doses are titrated to normal levels of T4, levels of circulating T3 do not reach normal physiological levels after T4 administration. By contrast, when doses are normalized using serum T3, T4 levels will be excessively high. Normal thyroid state (euthroid) in serum as well as in various tissues of a thyroidectomized rat required combined T3 and T4.

The importance of including T3 in regimens for treating mood disorders and other symptoms of clinical hypothyroidism has been examined. Evidence suggesting a need to include T3 with T4 is found, in part, in the observation that not all patients respond completely to T4 alone. In addition, the conversion mechanism in the brain—where a lack of T3 may be expected to result in mood disorders—is not the same as that in other tissues, such as in the liver. Although some patients prefer the combination for subjective reasons, this patient preference is balanced by the increased risk perceived to accompany the use of T3 stemming from a surge in serum levels of T3 following ingestion of a T3-containing formulation. Additional risks attributed to T3 relate to its short half-life (relative to T4) and its low therapeutic index. Thus, researchers have observed that once-daily administration of T3 does not prevent profound hypothyroidism and have indicated that a CR preparation of T3, which avoids the $C_{max}$ surge and provides steady T3 serum levels over 24 hours, will be necessary to adequately test the T3/T4 combination strategy. In fact, many physicians are reluctant to prescribe T3 therapies due to the risk that the drug will spike to toxic levels even at relatively low doses. Such spiking occurs because of rapid absorption of the drug resulting in high concentrations (above the therapeutic level) in the blood stream soon after administration.

Thyroid hormones are used cautiously due to the number of circumstances where the integrity of the cardiovascular system—particularly the coronary arteries—is suspected. In such cases, low-dose liothyronine sodium therapy is initiated with due consideration for its relatively rapid onset of action (T3 spiking and rapid absorption). A common starting dosage of CYTOMEL, for example, is 5 mcg daily, which is usually increased by no more than 5 mcg increments at 2-week intervals. In patients for whom an euthyroid state can be reached only at the expense of aggravating cardiovascular disease, thyroid hormone dosage is either reduced or eliminated entirely. As a result, T3 drugs are underutilized and patients who could greatly benefit from such therapy are deprived.

As described above, T3 is not a primary treatment regimen for thyroid-related disorders due to its high potency and concomitant rapid absorption in the small intestine. The rapid absorption of T3 stems, in part, from its dissolution kinetics in the intestinal lumen and the presence of highly efficient T3 transporters lining the intestinal epithelial cells. Accordingly, a CR preparation of T3 is desirable and can be provided in accordance with the present teachings. In some embodiments, a T3:metal complex is provided such that the absorption pharmacokinetics of T3 alone have been modulated and toxic levels are not reached while therapeutic levels are maintained for extended periods. In some embodiments, the metal is bismuth. In some embodiments, a combination of T4 and T3 in which T3 is provided in a CR formulation in accordance with the present teachings (e.g., as a bismuth:T3 complex) is used in the treatment of hypothyroidism.

Sufficient extension of the $t_{max}$ and lowering of the $C_{max}$ of T3 should improve the safety profile of CYTOMEL substantially. Converting T3 into a metal coordination complex in accordance with the present teachings is expected to provide the flexibility necessary to impart modulated pharmacokinetics for improved drug safety. Because metals, in general, are capable of coordinating 6 ligands, metal coordination in accordance with the present teachings allows for the incorporation of adjuvants into the T3:metal coordination complex. By way of example, if T3 occupies 4 ligand sites, there are 2 coordination sites still available for coordination to adjuvants. Moreover, representative adjuvants such as amino acids, peptides, carbohydrates and/or lipids can also be coordinated to a metallo-T3 compound to further enhance the desired plasma level-time curve. In some embodiments, combining metal coordination chemistry with gastroretentive technologies can dramatically alter the pharmacokinetics of T3.

In a third series of embodiments, the biologically active agent coordinated to a metal is mesalamine (5-aminosalicylic acid or 5-ASA). By way of introduction, ulcerative colitis is a chronic inflammatory disorder that primarily affects colonic mucosa. Aminosalicylates, such as mesalamine, remain the first-line therapy for both induction and remission of mild to moderate UC but typically require large multiple daily doses to effectively control the disease. These regimens place an onerous burden on afflicted patients and frequently lead to non-compliance and preventable exacerbations and complications, such as massive rectal bleeding, infection, ileus, and perforation. In the latter stages of UC, carcinoma of the colon can occur. Current therapeutic interventions—either FDA-approved or under investigation—include: small molecules (e.g., anti-inflammatories, such as aminosalicylates and corticosteroids; immunosuprresants such as cyclosporine, methotrexate, and mercaptopurine; PPAR activators such as rosiglitazone and aminosalicylates; antibiotics such as anti-fusobacterium; ICAM-1 Inhibitors; and transdermal nicotine); biologics (e.g., antibodies such as CD-3 antibodies, integrins, tropomysin isoforms, and TNF; interferon; colonic endothelial protein (CEP); hTM5 interacting protein; interleukin receptor protein; and low molecular weight heparin); and natural extracts (e.g., peony root).

A significant component of the dosing requirement for mesalamine stems from its inconsistent availability to the epithelia of the terminal ileum and colon—regions where the mucosa is typically inflamed in UC. Approximately 80% of colon-targeted mesalamine is eventually excreted in the stool with most unwanted systemic absorption occurring proximal to the terminal ileum. Additionally, mesalamine is poorly absorbed from the colon, which increases its ability to exert its anti-inflammatory effects on targeted mucosa. Delayed-release mesalamines, which exploit existing pH-gradients in the GI tract to facilitate delivery of 5-ASA to inflamed epithelia, may be less effective in some individuals due to a high variability in GI pH between patients as well as to a lower colonic pH in some individuals due to inflammation from active UC. Furthermore, mesalamine formulations requiring heavy pill burdens and inconvenient dosing regimens reduce patient adherence. This variability in the delivery of effective therapeutic levels of 5-ASA reduces drug efficacy and overall disease control, and increases the likelihood of clinical relapse.

A variety of drug delivery formulations have been developed in an attempt to overcome the poor patient compliance associated with 5-ASA administration. For example, pH-dependent release 800 mg tablets, micropellets, and a Multi Matrix System (MMX) such as that used in the product sold under the tradename LIALDA by Shire US Inc. are designed to provide once or twice daily dosing of a high strength tablet. However, the large size of the tablets in these delivery formulations still presents a challenge to patients who occasionally prefer to switch back to multiple doses of smaller tablets.

In spite of these advances in the treatment of UC, there is still a need to improve drug performance (e.g., by reducing dosing and improving therapeutic delivery). Modifying the long-term behavior of UC with early, aggressive management can successfully halt disease progression and reduce the risk of colon cancer. As with other autoimmune diseases, early suppression of the inflammatory cascade can both induce and maintain remission of the disease, thereby improving patients' quality of life by helping to preserve mucosal integrity and functioning.

The expressions of cell adhesion molecules are enhanced in endothelial cells in response to inflammation events, such as stimulation with TNF, IL or IFN. For example, colonic epithelial cells with UC synthesized IL-1. In addition, the expression of the mucosal addressin cell adhesion molecule-1 (MAdCAM-1) was induced in response to TNF stimulation in colon endothelial cells. The role that ICAMs play in inflammation is to allow the integrins and other bioadhesive reagents to bind to the cells expressing the ICAM, thereby causing secondary inflammation events. As further explained below, this property can be exploited using metal coordination chemistry.

In accordance with the present teachings, a novel method of delivering 5-ASA to the colon to increase its potency, thereby reducing the dose requirement, is provided. By targeting the drug to inflamed colonic mucosa, disease modification can occur. In some embodiments, these properties are imparted by binding 5-ASA to a metal ion to form a metal coordinated pharmaceutical, which is configured to minimize transport of drug across the duodenal membrane and deliver drug to the desired local site of action in the colon. Thus, in some embodiments, the absorption of mesalamine absorption into the bloodstream is prevented by virtue of its binding to a metal. In some embodiments, the metal is bismuth.

In some embodiments, the metallo-mesalamine complex possesses bioadhesive properties, which will have the effect of increasing potency by increasing residence time of mesalamine in the colon—thereby reducing dosing frequency. Furthermore, by reducing the dosing requirement, the amount of systemic mesalamine will likewise be reduced in a concentration-dependent manner.

Without wishing to be bound by a particular theory or to in any way limit the scope of the appended claims or their equivalents, it is presently believed that the bioadhesive properties of metallo-mesalamine can be imparted via the formation of a biofilm that adheres to colonic epithelia cells through a combination of bonding forces (e.g., lipophilic interactions, hydrogen bonding, Van der Waals forces, metal-ligand bonding, etc.). In some embodiments, the adhesive property of the metallo-mesalamine complex is facilitated by a polymeric structure of the metallo-mesalamine complex. In some embodiments, the metal is bismuth which—when coordinated to organic ligands—favors the formation of polymeric structures.

In some embodiments, bioadhesive agents are included as adjuvants in the 5-ASA:metal complex. In some embodiments, the bioadhesive agents are selected from a group of compounds that bind to ICAMs, such that delivery of the metallo:mesalamine:bioadhesive complex will be targeted to cells expressing ICAM, thereby allowing disease modification to occur. In some embodiments, increased potency of mesalamine is imparted through coordination of the mesalamine to a metal (with or without a bioadhesive adjuvant), which provides for increased residence time of mesalamine in the colon and/or targeted delivery of the drug to cells expressing ICAM. In some embodiments, the metal is bismuth, which can render the inclusion of a bioadhesive adjuvant ligand (e.g. ICAM binder) unnecessary inasmuch as sufficient bioadhesive properties are imparted through the polymeric structure of the bismuth:mesalamine.

Mesalamine coordination complexes of Bi, Al, Zn, Ba, Cu, Mg and Ca have been prepared. Due to the multiple coordination sites on the metal, bioadhesive adjuvants, such glucosamine or mannuronic acid, can be added to the coordination complex which allows the mesalamine complex to bind to ICAM, as shown in FIG. 1.

Figure 2:
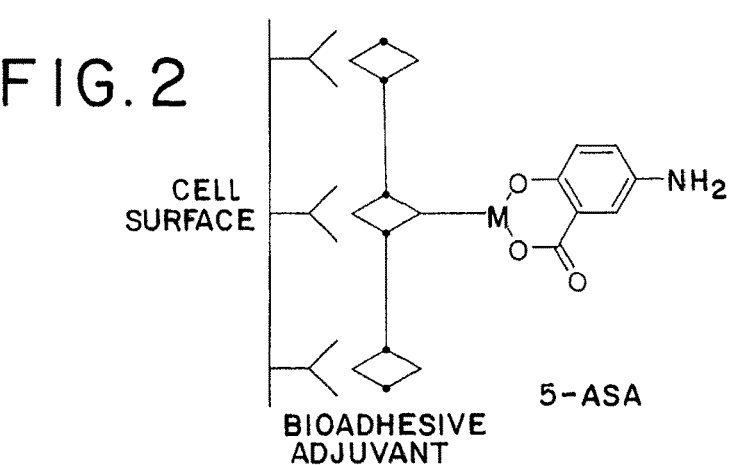
FIG. 2 shows a schematic illustration of a polymeric bioadhesive adjuvant coordinated to a monomeric metal-containing compound.

Bioadhesion strength is related to number of binding sites. Thus, for synthesized or designed bioadhesive reagents, a monomeric unit of a polymer will not have nearly the same bioadhesive properties as the polymer. For example, chitosan and alginic acid have much stronger bioadhesive properties than glucosamine and mannuronic acid, respectively. Accordingly, in some embodiments, polymeric bioadhesive reagents are incorporated into the metal coordination complex, thereby increasing bioadhesive properties and in turn the potency and residence time of mesalamine attached to the complex, as shown in FIG. 2. Due to bioadhesion, the attendant potency of this formulation is exchanged for decreased potency by molecular weight dilution.

Figure 3:
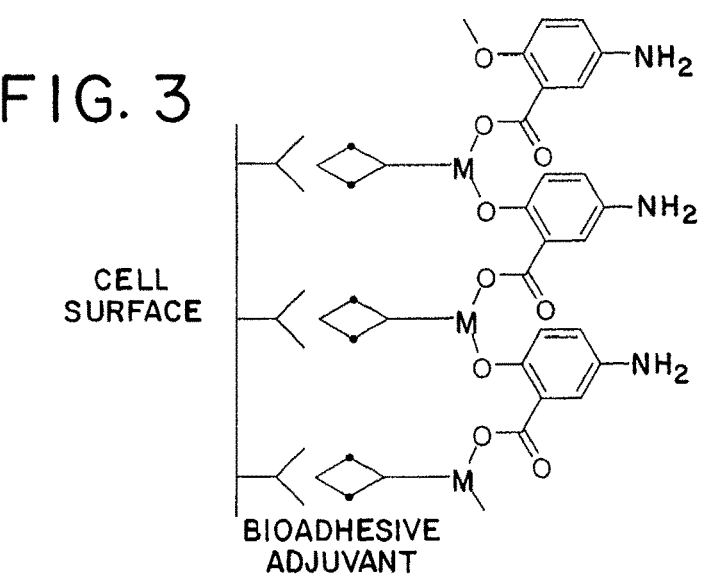
FIG. 3 shows monomeric bioadhesive adjuvants coordinated to a polymeric metal-containing compound.

Depending on the method of synthesis, metal coordination compounds in accordance with the present teachings can be either monomeric or polymeric. Thus, through the proper selection of a monomeric bioadhesive adjuvant (e.g. glucosamine, mannuronic acid, etc) and poly-metallo mesalamine (PMM), an optimal combination of polymeric bioadhesive properties and maximum dose strength can be achieved, as shown in FIG. 3.

In some embodiments, the metal in the metal:mesalamine complex is bismuth. A first benefit in using bismuth as the metal is that it has direct activity in treating colitis. For example, treatment with bismuth-containing enemas was found in small clinical studies to be beneficial in patients with left-sided colitis and pouchitis. A second benefit is that when applied as a complex with certain organic acids, bismuth is known to form building blocks that assemble into a three-dimensional polymer, which can improve mesalamine's application and retention to the inflamed colon. Thus, in some embodiments, the formation of polymeric biofilms containing both bismuth and mesalamine creates an adhesive covering for colonic epithelial tissue and promotes re-establishment of physiologic bacterial biofilms that can decrease inflammation and control colitis better than existing products in patients with UC.

In a fourth series of embodiments, the biologically active agent coordinated to a metal is dichloroacetate. By way of introduction, acetic acid is a well-known component of vinegar that is obtained, for example, from the bacterial fermentation of beer, cider, and wine. It is a basic building block of biochemistry since acetyl groups are commonly found in many biological molecules. Moreover, the movement of acetyl groups between molecules is involved in many life processes. Thus, the dichlorinated derivative of acetic acid—namely, DCA—has medicinal potential. Without wishing to be bound by a particular theory or to in any way limit the scope of the appended claims or their equivalents, it is presently believed that DCA can be useful as a treatment for cancer since it alters biochemical processes that transfer energy through metabolism within all cells. By inducing cancer cells to reverse the "Warburg effect" (i.e., the reliance by tumor cells on anaerobic glycolysis even when oxygen is freely available), it is presently believed that DCA may promote apoptosis leading to selective cell death in tumors. However, DCA produces a dose-related peripheral neuropathy, and drug development for this molecule has been slow.

There is growing evidence to suggest that mitochondria may be primary targets of cancer therapeutics as opposed to mere bystanders during cancer development—a distinction that can be explained based on the Warburg effect. To understand the concept of the Warburg effect, it is helpful to comprehend how cells in the body convert food (e.g., glucose) into the chemical forms of energy that are used as biochemical currency. Cells normally use oxidative phosphorylation within the mitochondria (Krebs Cycle and the electron transport chain) to complete the breakdown of glucose that starts in the cytosol. This maximizes the efficiency of certain redox reactions and the formation of high-energy bonds within molecules like ATP, which act as energy currency throughout the body. In the absence of oxygen, cells extract the energy of glucose through a much less efficient process that finishes glycolysis in the cytosol with lactic acid as the final metabolite. Although the oxidative process is far more efficient, anaerobic glycolysis is useful at times of oxygen deprivation.

By relying heavily on less efficient glycolysis, cancer cells develop more efficient mechanisms for glucose uptake to compensate for the lost efficiency of the aerobic process. This "metabolic remodeling" may be involved in making cells independent of normal regulators of cell growth. Thus, the Warburg effect may be necessary for a normal cell to transform into a cancer cell since normal mechanisms of programmed cell death (apoptosis) can now be avoided. Rather, the cell becomes independent of the environment for nutrient uptake, steadily producing energy to drive uncontrolled growth.

Without wishing to be bound by a particular theory or to in any way limit the scope of the appended claims or their equivalents, it is presently believed that the mechanism of action for DCA involves pyruvate, the key metabolite of cytosolic glycolysis, which needs to enter the mitochondrion in order to finish the process oxidatively. When the pyruvate dehydrogenase (PDH) enzyme complex (which catalyzes the decarboxylation of pyruvate) is activated, more pyruvate enters the mitochondria from the cytosol. The activity of PDH is regulated by a phosphorylation reaction catalyzed by pyruvate dehydrogenase kinase (PDK). By inhibiting the PDKII isozyme, DCA locks the enzyme complex in its unphosphorylated and active form.

Although DCA is generally 100% absorbed in high orally administered doses, some researchers have observed large variations (e.g., 27% to 100%) in DCA bioavailability between individuals at lower doses. In addition, DCA is able to inhibit its own metabolism in rodents and humans across a large range of concentrations—an effect that is more pronounced in adults than in children. At the same time, adult rodents, dogs, and humans experience a higher incidence of reversible peripheral neuropathy than young individuals following DCA administration. Thus, apparently as a result of self-inhibition of its metabolism, higher blood levels of DCA result, which lead to increased peripheral neuropathy. Without wishing to be bound by a particular theory or to in any way limit the scope of the appended claims or their equivalents, it is presently believed that this neurotoxic effect may be related to the age-dependent formation and accumulation of monochloroacetate (MCA), a metabolic product of DCA which is known to be toxic to neurons.

Although the peripheral neuropathy observed in clinical studies of DCA has led some researchers to reject DCA as a viable drug candidate, it is believed that metal coordination of DCA in accordance with the present teachings can improve its undesirable PK properties rendering it useful for therapeutic application.

Metal coordination of DCA in accordance with the present teachings provides a mechanism for improving absorption of the drug so that constant and predictable plasma levels of the drug can be attained. Maintaining plasma DCA concentrations at optimum levels for anti-neoplastic activity, and below those required to induce peripheral neuropathy, should improve the drug's therapeutic potential. In some embodiments, a metal:DCA complex provides a more slowly absorbed dose with greater control of maximum serum concentration in children and adults, thereby allowing fewer incidents of peripheral neuropathy and helping restore balance to the risk/benefit ratio for this drug. In some embodiments, the metal is bismuth.

Coordination compounds of bismuth typically have poor solubilities in most organic solvents and water, such that definitive structural assignments are often based on X-ray diffraction studies of available crystalline samples. However, because of the large range of coordination numbers available to Bi (e.g., 2 through 10) and the polydentate character of many organic ligands, complex three-dimensional molecular arrays and clusters are often obtained for bismuth complexes even for what appear to be relatively simple stoichiometric compounds. Furthermore, many compounds of bismuth readily undergo hydrolysis in water to afford compounds incorporating the Bi(O) functionality. By way of example, colloidal bismuth subcitrate (CBS, such as that sold under the tradename DE-NOL by Astellas Pharma Europe BV), a drug used clinically in the treatment of *Helicobacter pylori* infection, has at least six known structures depending on the crystallization conditions.

According to HSAB (Hard Soft Acid Base) theory, Bi(III) is a soft metal ion and, as such, has a high affinity for both oxygen and nitrogen ligands in aqueous solution. Biologically active agents for use as ligands in accordance with the present teachings include but are not limited to carboxylic acids, hydroxyl-carboxylic acids, and amino acids—each of which is known to form complexes with bismuth. Five representative generalized synthetic procedures for the preparation of bismuth coordination compounds are shown in reactions (1)-(5) below. As a matter of interest, reaction (2) was adopted to prepare $Bi(dopa)_3$, as further described in the examples below.

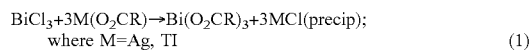

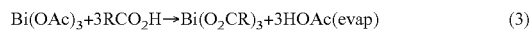

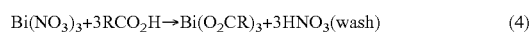

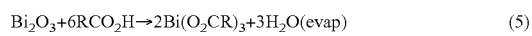

Figure 4:
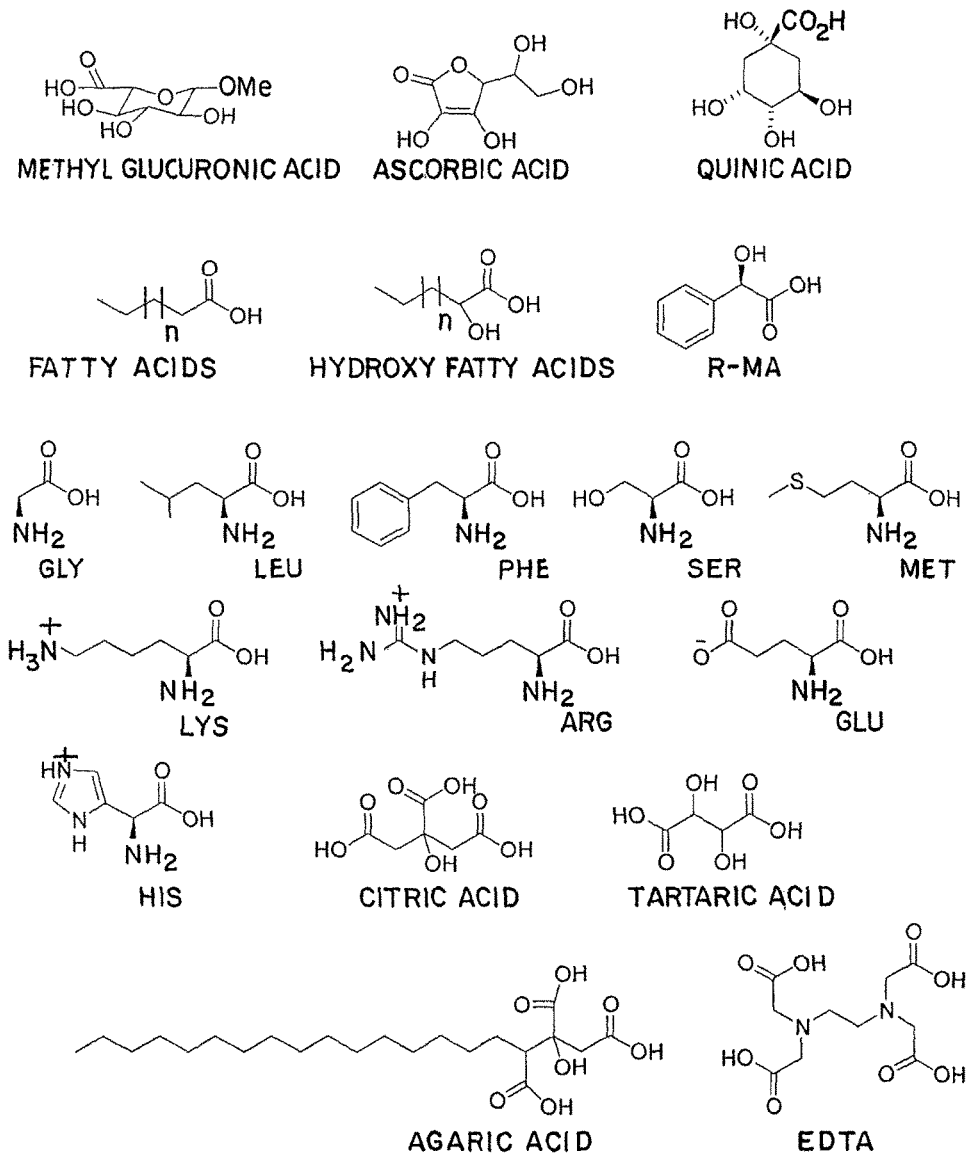
FIG. 4 shows molecular structures for representative adjuvant ligands for use in metal-containing compounds.

In addition to simpler coordination complexes expected from various combinations of bismuth and a biologically active agent, the present teachings also encompass examples of mixed ligand or ternary coordination complexes, in which two or more different ligands occupy the first coordination sphere. In such compounds, an adjuvant is substituted for at least one of the three drug molecules in the products shown in Equations (1)-(5) above. In some embodiments, the adjuvant is chosen from a group of biologically safe chelating agents that includes but is not limited to lipids, amino acids, carbohydrates, bioadhesive polymers, peptides, and the like. Molecular structures of representative adjuvants are shown in FIG. 4. In some embodiments, these adjuvants enhance gastric retention and/or improve the steady-state PK properties of a drug coordinated to bismuth.

Figure 5:
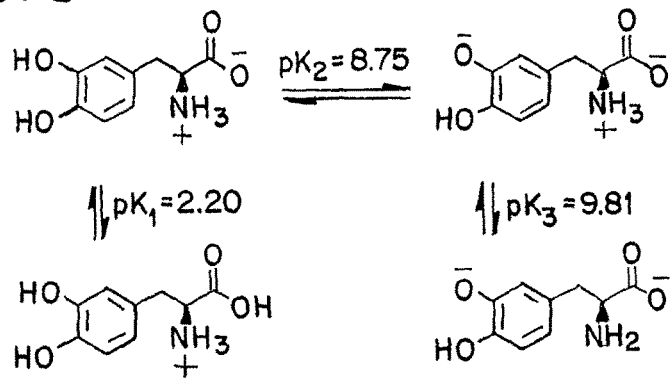
FIG. 5 shows $PK_a$ values and coordination sites for LD.
Figure 6:
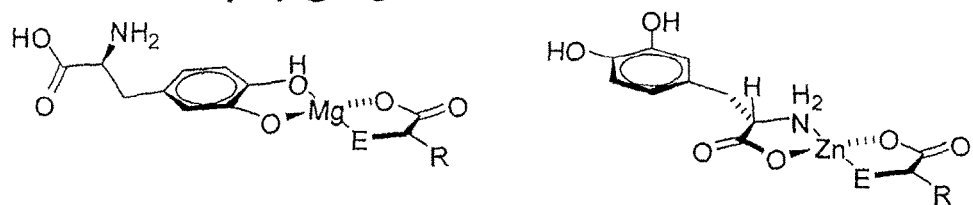
FIG. 6 depicts catechol coordination vs. amino acid coordination in two LD coordination compounds (wherein E represents $NH_2$, OH or H).

In accordance with the present teachings, a bismuth-containing compound that contains bismuth, LD, and an adjuvant selected from the group consisting of lipids, carbohydrates, amino acids, bioadhesive polymers, and peptides is provided. In preparing LD-containing coordination complexes in accordance with the present teachings, it is helpful to bear in mind certain features of LD. First, oxidative lability of LD can result in the formation of unwanted quinone by-products due to reaction of LD with molecular oxygen—a reaction that can be catalyzed by impurities present in reaction solvents. Second, as shown in FIG. 5, LD has three protonation sites, which correspond, respectively, to carboxylate, meta-phenol, and amino group. Accordingly, two different sites of chelation—amino acid and catechol—are possible, as shown in FIG. 6, and products arising via coordination at these sites can be differentiated using $^1$H-NMR spectroscopy. The actual site of chelation is strongly dependent on metal (e.g., Mg demonstrates a preference for catechol chelates, whereas Zn favors formation of amino acid coordination compounds) and less dependent on actual $pK_a$ values of unchelated LD (the $pK_a$ values of ligands can be shifted 2-3 log units downward as coordination occurs due to stabilization of incipient anionic charge by the positive metal ion).

Figure 7:
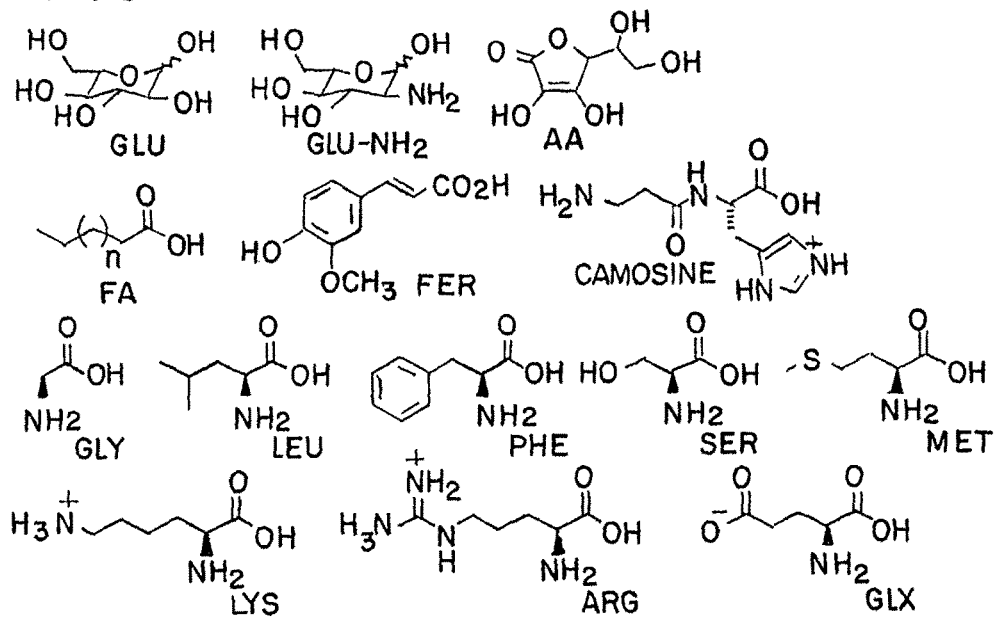
FIG. 7 shows molecular structures for representative adjuvant ligands for use in bismuth-containing compounds (particularly, though not exclusively, one that contains LD).

Typically, metals can accommodate six coordinated ligands but for bismuth the coordination number ranges from 2 to 10. By virtue of its catechol and amino acid moieties, LD is likely to be a bidentate ligand and, therefore, is configured to occupy 2 or 4 coordination sites on a metal, thereby leaving 2-4 additional coordination sites on the metal for binding with other ligands or adjuvants. In some embodiments, these adjuvants are designed to enhance the properties of the metal:LD coordination complex and, in some embodiments, are selected from lipids, carbohydrates, amino acids, bioadhesive polymers, peptides, and the like. FIG. 7 shows representative examples of monomeric adjuvants for use in metal:LD:adjuvant coordination complexes in accordance with the present teachings. In some embodiments, both the adjuvant and LD are bound to the same metal. In some embodiments, the metal is bismuth.

In some embodiments, the adjuvant is an amino acid. Due to the powerful chelating abilities, commercial availability, and diverse physicochemical properties of this group of adjuvants, amino acids are versatile candidates for incorporation into metal:LD complexes in accordance with the present teachings. Moreover, amino acid adjuvants can be expected to enhance the amphiphilic properties and stabilities of coordination complexes in accordance with the present teachings. Representative amino acids for use as adjuvants in accordance with the present teachings are shown in FIG. 7 and include aliphatic, aromatic, cationic, anionic, and polar compounds. In some embodiments, a compound in accordance with the present teachings contains an amino acid, a metal, and LD bound together in a coordination complex. In some embodiments, the amino acid adjuvant is arginine or glycine. In some embodiments, the metal is bismuth.

In some embodiments, the adjuvant is a lipid or fatty acid (abbreviated FA in FIG. 7). In some embodiments, a compound in accordance with the present teachings contains a lipid, a metal, and LD bound together in a coordination complex. In some embodiments, the lipid adjuvant is ferulic acid (abbreviated "fer" in FIG. 7). In some embodiments, the metal is bismuth.

In some embodiments, the adjuvant is a bioadhesive polymer. Without wishing to be bound by a particular theory or to in any way limit the scope of the appended claims or their equivalents, it is presently believed that by incorporating a bioadhesive polymer adjuvant in a metal:LD complex in accordance with the present teachings, a portion of the dose can be retained upstream from the duodenum (e.g., gastroretention). In such a way, LD will slowly dissociate from the complex and pass through the site of absorption in a manner that will extend its absorption phase, thereby helping maintain plasma LD levels at later times in accordance with the CDS objective. In some embodiments, a compound in accordance with the present teachings contains a bioadhesive polymer, a metal, and LD bound together in a coordination complex. In some embodiments, the metal is bismuth. Representative bioadhesive polymers for use as adjuvants in accordance with the present teachings include but are not limited to alginic acid/sodium alginate, chitosan, chitin, polyacrylic acids, pectin, pullulan, hydroxypropylmethylcellulose (HPMC), and the like. In some embodiments, the bioadhesive polymer adjuvants are chitin or chitosan, which have particularly strong affinities for metals and are readily modified by chemical modification.

Representative metals for use in coordinating to LD in accordance with the present teachings include but are not limited to all transition metals, p-block metals, and s-block metals. In some embodiments, the metal is selected from the group consisting of iron, magnesium, calcium, zinc, copper, and bismuth. In some embodiments, the metal is bismuth.

Without wishing to be bound by a particular theory or to in any way limit the scope of the appended claims or their equivalents, it is presently believed that by increasing the availability of LD to the brain and by lowering inter- and intra-subject variabilities, metal:LD complexes in accordance with the present teachings may be resistant to extracerebral decarboxylation. In addition, by providing an LD formulation that is less susceptible to decarboxylation, the amounts of carbidopa needed for co-administration in advanced PD patients can be decreased, thereby reducing the impact of possible BBB dysfunction on CNS function.

In order to fully optimize anti-PD treatment it is necessary to "tune" all the variables that affect the plasma LD level— time curve. This includes having enough carbidopa present in the plasma to continuously protect peripheral plasma LD (i.e., not yet in the brain) from premature decarboxylation. In other words, once the LD is absorbed into the systemic circulation, it is desirable to prevent its conversion to dopamine before it gets into the brain. Standard methods for preventing peripheral decarboxylation typically involve the use of carbidopa, which is administered with LD orally. Recent studies indicate that this method is not always optimized since the plasma levels of carbidopa and the duration of enzyme inhibition can vary between individuals. Thus, in some embodiments, carbidopa is coordinated with metal to achieve a sustained-release effect, thereby preventing a situation where LD is present in the plasma but carbidopa levels are no longer effective. In some embodiments, the sustained pharmacokinetics of carbidopa as a function of its release from the metal coordination complex provide a steady state concentration of carbidopa in the blood stream, such that prevention of LD decarboxylation is optimized. In some embodiments, other metal coordinated aromatic amino acid decarboxylase inhibitors are provided.

As further described in the examples below, various metal coordination complexes of LD have been prepared. A representative general procedure for the preparation of these homoligated metal chelates involves treating solutions of L-DOPA in a suitable solvent (including but not limited to water, methanol, DMSO, and DMAC) with a base (including but not limited to $NaHCO_3$, $K_2CO_3$, NaOH, KOH, LiOH, $Ca(OCH_3)_2$, potassium tert-butoxide, and $Et_3N$) and a metal salt (including but not limited to chlorides, acetates, and metal oxides). The resultant compounds are tested for authenticity using proton nuclear magnetic resonance ($^1H$ NMR) spectroscopy, mass spectrometry, and/or metals analysis.

In the preparation of a coordination complex that contains an adjuvant, parameters such as stoichiometry, order of reagent addition, solvent, temperature, concentration, purity of solvents and/or reagents, and the like should be controlled. Within these parameters, the preparation of a coordination complex that contains an adjuvant can be achieved by a synthetic route including but not limited to the following, as depicted schematically in the corresponding reactions (6)-(9) below: (6) simultaneous combination of the biologically active agent (L) and adjuvant (L'); (7) sequential combination of the ligands L and L'; (8) reproportionation reaction between two binary bis-ligand (or homoleptic) complexes; and (9) substitution reaction in which a ligand in a metal complex is replaced by a second ligand (a reaction that depends on thermodynamic stability of the ligand binding with the metal ion and on the reaction mechanism).

  (6)

  (7)

  (8)

  (9)

In a solution containing a metal ion and ligands L and L', the formation of the mixed ligand complex MLL' is more favored on a statistical basis than the formation of the binary complexes $ML_2$ and $ML'_2$. The equilibrium constant for the formation of the mixed ligand complex is related to the equilibrium constant of the corresponding reproportionation reaction (reaction 8 above), $K_{reprop}$. If statistical factors alone were responsible for formation of the mixed ligand complex, then $K_{reprop}$ would equal 4. However, since the experimental values of $K_{reprop}$ differ from the statistical value, other factors are involved in the formation of mixed ligand complexes. These factors include electronic, electrostatic, and steric effects that can affect product formation by stabilizing or destabilizing the complexes.

As an initial test of the synthetic protocols, metal:LD: amino acid complexes employing all four of the above reaction schemes (6)-(9) have been successfully prepared. In some embodiments, a method according to reaction (6) (viz., the simultaneous combination of two ligands) is presently desirable. Generally, an aqueous solution of LD and an amino acid is reacted with 1 equivalent of $Ba(OH)_2$. Next, a metal sulphate is added. The $Ba(SO_4)_2$ precipitate is filtered and the solution is concentrated leaving the crude metal:LD:amino acid complex. To minimize the problem of LD oxidation, only thoroughly degassed reagent grade water is used.

In embodiments in which a bioadhesive polymer adjuvant is to be incorporated into the complex, a method according to reaction 7—whereby the metal and LD are sequentially coordinated followed by coordination to the bioadhesive polymer—is presently desirable. The plasma level-time curve of LD can be "fine-tuned" through a variety of chemical modifications to the bioadhesive polymer adjuvant (including but not limited to acetylation, pH, molecular weight distribution of the polymer, and the like, and combinations thereof) and to the method of preparation (e.g., inner vs. outer sphere coordination, solvent, temperature, reagents employed, concentration, and the like, and combinations thereof). In some embodiments, the bioadhesive polymer is chitosan, the free amino groups of which provide considerable flexibility. For example, lipophilicity can be controlled by adding longer chain fatty acid anhydrides or the amino groups can be converted to carboxyl groups with the addition of succinic anhydride. In addition, the penetrability of the bioadhesive polymer can be modulated by controlling its rigidity—for example, by including double bonds in the adjuvant. For terminal carboxylic acid groups, this can be achieved through the addition of maleic anhydride.

The results of PK studies in rats plotted as plasma level vs. time curves revealed tris(LD)bismuth oxide [Bi(O)(dopa)$_3$] with a lower $C_{max}$, a later $t_{max}$, and a longer duration within the hypothetical therapeutic window than LD/carbidopa. These studies demonstrate—perhaps for the first time—that the pharmacokinetics of LD can be significantly enhanced at the molecular level without recourse to covalent modification of the parent drug and/or formulation techniques.

As can be appreciated from the description above, a key advantage in accordance with the present teachings is the relative ease of synthesizing the coordination complexes. Thus, scaling up a synthetic protocol to kilogram-sized batches is not expected to present undue difficulties.

In some embodiments, coordination polymers in accordance with the present teachings are prepared through a self-assembly of metal ions and biologically active agents (i.e., organic ligands) having appropriate functionalities. The strength of coordination between a metal and the biologically active agent, the stereochemistry of the biologically active agent, the coordination number and geometry associated with the metal, and/or various other intermolecular interactions (e.g., Van der Waals interactions, hydrogen bonding, π-bonding, lipid-lipid interactions, etc.) can lead to diverse supramolecular geometries of one-, two-, and three-dimensional networks referred to herein as "coordination polymers" and also known as metal organic frameworks (MOFs).

The metal centers of these coordination polymers can be metal atoms, ions or clusters. In some embodiments, the metal centers are Bi(III) or BiO(I). In some embodiments, the coordination number of bismuth ranges from 2 to 10. In some embodiments, the biologically active agent in the coordination polymers is an organic ligand including but not limited to LD. For example, as shown in FIG. 5, LD has three protonation sites: carboxylate, meta-phenol, and amino. As a result, two different chelation sites (viz., the amino acid and catechol) are available for coordinating to a metal. Since bismuth is known to form complexes with both of these functional groups, complex three-dimensional molecular arrays can result from bismuth compounds containing LD.

The following examples and representative procedures illustrate features in accordance with the present teachings, and are provided solely by way of illustration. They are not intended to limit the scope of the appended claims or their equivalents.

EXAMPLES

General Synthetic Protocol and Spectroscopy: Stable metal complexes were prepared as described below. The proposed structures of compounds were based on the $^1$H NMR spectrum, with the location of chelation being determined from observed changes in chemical shifts and line broadening, theoretical calculations from known coordination complexes of similar composition, and mass spectrometric data. Note, for comparison purposes, the proton NMR spectrum of DOPA is ($^1$H NMR, D$_2$O): δ 6.90 (d; J=8.2 Hz; 1 H), 6.82 (d; J=2.2 Hz, 1 H), 6.74 (dd; J=8.2 Hz, J=2.2 Hz; 1 H), 3.92 (dd; J=7.8 Hz, J=5.2 Hz; 1 H), 3.16 (dd; J=14.6 Hz, 5.2 Hz; 1 H), 2.99 (dd; J=14.6 Hz, 7.8 Hz; 1 H). The metal coordination complexes were neither salts nor mixtures as indicated by the stabilities observed on solid phase extraction (SPE) columns. Magnesium salts and zinc salts are not retained on the SPE column while LD is retained much more tightly on the SPE column than the metal coordination complexes.

Synthesis of Mg(dopa)$_2$: To a 100-mL round-bottomed flask equipped with magnetic stirrer and N$_2$ inlet were added levodopa (1.00 g, 5.07 mmol) and anhydrous dimethyl acetamide (DMAC, 50 mL). A solution of potassium tert-butoxide in tetrahydrofuran (THF) (1.00 M, 5.07 mL, 5.07 mmol) was added dropwise via syringe. The solution was stirred for 15 minutes and solid MgCl$_2$ (243 mg, 2.54 mmol) was added in one portion. Stirring was continued overnight.

Solvent was removed under reduced pressure leaving a tan solid that was purified by SPE using a 20 cc (1 g) Oasis HLB cartridge (Waters). Both the water and methanol SPE solvents were degassed to prevent oxidation of the chelate. The product was eluted with 5% MeOH/$H_2O$ (levodopa elutes with 20% MeOH/$H_2O$). Solvent was removed under reduced pressure leaving 1.022 g (2.44 mmol, 96%) of an off-white solid. A $^1$H NMR of this material was obtained indicating formation of the catechol chelate as shown below. $^1$H NMR ($D_2O$): δ 6.78 (br d; 1H), 6.71 (br s; 1H), 6.61 (br m; 1H), 3.85 (dd; J=8.0 Hz; J=5.0 Hz; 1H), 3.11 (dd; J=14.4 Hz; J=5.0 Hz; 1H), 2.91 (dd; J=14.4 Hz; J=8.0 Hz; 1H).

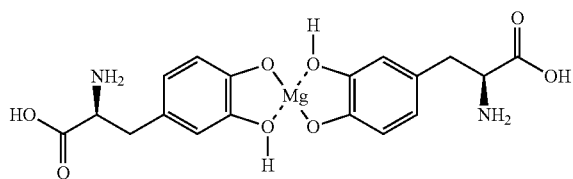

Synthesis of Zn(dopa)$_2$: To a 500-mL round-bottomed flask equipped with $N_2$ inlet and magnetic stirrer, were added $K_2CO_3$ (67 mg, 0.44 mmol), $H_2O$ (degassed for 1 hour under aspirator vacuum prior to use, 200 mL), and levodopa (1.00 g, 5.07 mmol). The mixture was gently heated to effect dissolution. Zinc oxide (208 mg, 2.54 mmol) was added and stirring continued overnight. The reaction turned cloudy. Purification was by SPE as above. The product eluted with 5% MeOH/$H_2O$, Solvent was removed on a rotary evaporator leaving 650 mg (1.41 mmol, 56%) of a light brown solid. A $^1$H NMR of this material was obtained indicating formation of the (amino acid) chelate as shown below. $^1$H NMR ($D_2O$): δ 6.87 (d; J=8.4 Hz; 1H), 6.80 (s; 1H), 6.70 (d; J=8.4 Hz; 1H), 3.87 (br s; 1H), 3.14 (dd; J=14.4 Hz; J=5.0 Hz; 1H), 2.95 (dd; J=14.4 Hz; J=8.0 Hz; 1H). Note: Slight line broadening was observed in the aromatic region and for H3 of the chelate. Significant line broadening was observed for H2 (ca 12 Hz at ½ peak height).

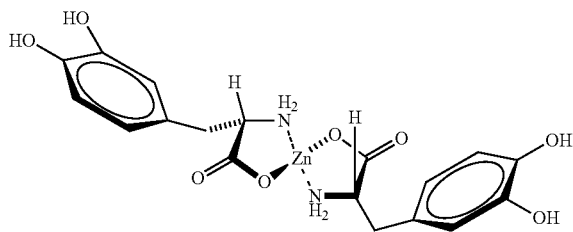

Synthesis of Mg(dopa)(gly): To a two-necked 200-mL round-bottomed flask equipped with a magnetic stirrer, heating mantle, reflux condenser, and $N_2$ inlet were added levodopa (500 mg, 2.54 mmol) and L-glycine (190 mg, 2.54 mmol). Water (100 mL) was added and the mixture was heated until the solids dissolved. Barium hydroxide (478 mg, 2.54 mmol) was added in one portion. The orange solution was stirred for 15 min at room temperature, and $MgSO_4$ (335 mg, 2.54 mmol) was added in one portion. A precipitate of $BaSO_4$ formed immediately. The light gray suspension was stirred an additional 1 hour, and heated at reflux for 1.5 hours. The mixture was cooled and vacuum filtered using medium porosity filter paper. Solvent was removed under reduced pressure leaving a light tan solid (638 mg, 2.17 mmol, 85%). $^1$H NMR ($D_2O$): δ 6.68 (br d; J=7.2 Hz; 1 H), 6.61 (br s; 1 H), 6.51 (br d; J=5.6 Hz; 1 H), 3.81 (dd; J=8.2 Hz, J=5.0 Hz; 1 H), 3.49 (s, 2 H), 3.07 (dd; J=14.3 Hz, 5.0 Hz; 1 H), 2.86 (dd; J=14.3 Hz, 8.2 Hz; 1 H).

Synthesis of Zn(dopa)(thr): To a two-necked 200-mL round-bottomed flask equipped with magnetic stirrer, heating mantle, reflux condenser, and $N_2$ inlet were added levodopa (500 mg, 2.54 mmol) and L-threonine (302 mg, 2.54 mmol). Water (100 mL) was added and the mixture was heated until the solids dissolved. Barium hydroxide (478 mg, 2.54 mmol) was added in one portion. The orange solution was stirred for 15 minutes at room temperature and $ZnSO_4$ (728 mg, 2.54 mmol) was added in one portion. A precipitate of $BaSO_4$ formed immediately. The light gray suspension was stirred an additional 1 hour and heated at reflux for 1.5 hours. The mixture was cooled and vacuum filtered using medium porosity filter paper. Solvent was removed under reduced pressure leaving a light gray solid (542 mg, 1.09 mmol, 86%). $^1$H NMR($D_2O$): δ 6.88 (br d; J=7.8 Hz; 1 H), 6.81 (br s; 1 H), 6.71 (br d; J=7.8 Hz; 1 H), 4.36 (br m; 1 H), 3.82 (br s; 1 H), 3.44 (br s; 1 H), 3.13 (br dd; J=14.0 Hz, 4.0 Hz; 1 H), 2.94 (br dd; J=14.0 Hz, 7.2 Hz; 1 H), 1.31 (d, J=6.4 Hz, 3 H).

Synthesis of Zn(dopa)(arg): To a two-necked 200-mL round-bottomed flask equipped with a magnetic stirrer, heating mantle, reflux condenser, and $N_2$ inlet were added levodopa (500 mg, 2.54 mmol) and L-arginine (440 mg, 2.54 mmol). Water (100 mL) was added and the mixture was heated until the solids dissolved. Barium hydroxide (478 mg, 2.54 mmol) was added in one portion. The orange solution was stirred for 15 minutes at room temperature and $ZnSO_4$ (335 mg, 2.54 mmol) was added in one portion. A precipitate of $BaSO_4$ formed immediately. The light orange suspension was stirred an additional 1 hour and heated at reflux for 1.5 hours. The mixture was cooled and vacuum filtered using medium porosity filter paper. Solvent was removed under reduced pressure leaving a tan solid (685 mg, 1.58 mmol, 62%). $^1$H NMR ($D_2O$): δ 6.75 (br d; J=7.6 Hz; 1 H), 6.68 (br s; 1 H), 6.55 (br 6; J=5.6 Hz; 1 H), 3.80 (br m; 1 H), 3.61 (t; J=5.6 Hz; 1 H), 3.21 (t; J=6.8 Hz; 2 H), 3.08 (dd; J=14.0 Hz, 3.2 Hz; 1 H), 2.88 (dd; J=14.0 Hz, 9.2 Hz; 1 H). 1.87-1.78 (m; 2 H), 1.71-1.60 (m; 2H).

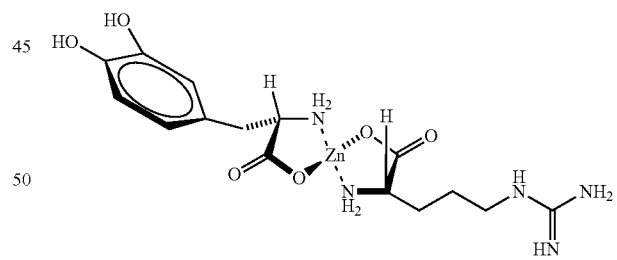

Synthesis of Sr(dopa)$_2$: To a 50-mL round-bottomed flask equipped with magnetic stirrer and $N_2$ inlet was added levodopa (90 mg, 0.46 mmol). Water (25 mL) was added and the mixture was heated until the solid dissolved. Strontium hydroxide (27.8 mg, 0.23 mmol) was added in one portion. The orange solution was stirred 30 minutes at room temperature. $^1$H NMR ($D_2O$): δ 6.77 (d; J=8.0 Hz; 1H), 6.68 (d; J=2.2 Hz; 1H), 6.56 (dd; J=8.0 Hz; J=2.2 Hz; 1H), 3.70 (dd; J=7.8 Hz; J=5.0 Hz; 1H), 3.02 (dd; J=14.4 Hz; J=5.0 Hz; 1H), 2.82 (dd; J=14.4 Hz; J=7.8 Hz; 1H).

Synthesis of Ca(dopa)$_2$: To a 100-mL round-bottomed flask equipped with magnetic stirrer and $N_2$ inlet was added levodopa (250 mg, 1.27 mmol). Water (50 mL) was added and the mixture heated until the solid dissolved. Calcium methoxide (65 mg, 0.634 mmol) was added in one portion. The orange solution was stirred for 3 hours at room temperature. Solvent was removed under pressure leaving brown solid. $^1$H NMR (D$_2$O): δ 6.75 (d; J=7.8 Hz; 1H), 6.67 (d; J=1.8 Hz; 1H), 6.56 (dd; J=7.8 Hz; J=1.8 Hz; 1H), 3.72 (dd; J=7.8 Hz; J=4.8 Hz; 1H), 3.02 (dd; J=14.0 Hz; J=4.8 Hz; 1H), 2.82 (dd; J=14.0 Hz; J=7.8 Hz; 1H).

Synthesis of bismuth dichloroacetic acid: Dichloroacetic acid (200 mg, 1.56 mmol) and toluene (15 mL) were added to a glass tube. After dissolution, triphenylbismuth (229 mg, 0.52 mmol) was added in one portion. The solution was heated to 100° C. and stirred for 18 hours. Solvent was removed under reduced pressure leaving a tan solid. $^1$H NMR (DMSO): δ 6.36 (s; 1H). Dichloroacetic acid $^1$H NMR (DMSO): δ 6.70 (s: 1H).

Synthesis of bismuth dopate, Bi(dopa)$_3$: To a 500-mL round-bottomed flask equipped with a N$_2$ inlet and magnetic stirrer were added dopaH (3.00 g, 15.2 mmol) and anhydrous DMSO (300 mL). The mixture was heated to effect dissolution and powdered Bi(NO$_3$)$_3$.5H$_2$O (2.46 g, 5.08 mmol) was added in one portion while the solution was still hot. After the solution cooled to room temperature, potassium tert-butoxide in butanol (15.2 mL, 15.2 mmol, 1 N) was added. A precipitate formed immediately. The mixture was stirred for 16 hours at room temperature. The reaction was filtered thru a medium glass frit and the product was washed with anhydrous methanol (2×50 mL) to afford a tan solid. This material was dried under vacuum (25° C., 2 torr) to afford 3.32 g (4.16 mmol, 82%) of Bi(dopa)$_3$. Approximately 3 mg of this material was dissolved in concentrated HNO$_3$, diluted with H$_2$O (20 mL), and titrated with EDTA (0.001 M) using xylenol orange tetra sodium as an indicator to determine bismuth content. The amount of bismuth found was 25.6% (26.2% based on Bi(dopa)$_3$). A sample was submitted for elemental analysis. Found: Bi, 46.8; C, 23.26; H, 2.68; N, 2.71; Calculated: Bi, 47.6; C, 24.61; H, 2.75; N, 3.19;

Synthesis of Bi(O)(dopa)$_3$: To a 1000-mL round-bottomed flask equipped with nitrogen inlet and magnetic stirrer were added levodopa (2.00 g, 10.2 mmol) and freshly degassed water (400 mL). Bismuth acetate (1.31 g, 3.38 mmol) was ground in a mortar and pestle, and added in one portion with stirring. The mixture was stirred for 3 hours at room temperature. Solvent was removed under reduced pressure leaving a pale yellow solid, which was dried under vacuum (2 torr, room temperature) for 24 hours. Analysis for Bi was obtained. Found: 23.1%. Calculated for Bi(O)(dopa)$_3$-4H$_2$O, 23.5%.

Synthesis of zinc mesalamine, Zn(mes)$_2$: To a 10-mL round-bottomed flask was added mesalamine (mesH) (1 g, 6.53 mmol). Aqueous sodium hydroxide (6.53 ml, 1 M, 6.53 mmol) was added by pipette and the solid dissolved. To a separate 25-ml round-bottomed flask equipped with magnetic stirrer were added zinc chloride (445 mg, 3.27 mmol) and water (1 ml). The aqueous mesalamine solution was added by pipette to the zinc chloride solution. The tan solution was stirred for 16 hours. The solution was vacuum filtered yielding a tan solid, which was dried under reduced pressure yielding 1.084 g (2.92 mmol, 89.1% yield). $^1$H NMR (DMSO-d$_6$): δ 12.01 (br s; 1 H), 7.11 (br d; J=2.2 Hz; 1 H), 6.66 (dd; J=8.6 Hz, 2.2 Hz; 1 H), 6.41 (br d; J=8.6 Hz; 1 H); 4.56 (br s; 2 H).

Preparation of calcium mesalamine, Ca(mes)$_2$: To a 10-mL round-bottomed flask was added mesalamine (1.00 g, 6.53 mmol). Aqueous sodium hydroxide (6.53 ml, 1 M, 6.53 mmol) was added by pipette and the solid dissolved. To a separate 25-ml round-bottomed flask equipped with magnetic stirrer was added calcium chloride (362 mg, 3.27 mmol) and water (1 ml). The aqueous mesalamine solution was added by pipette to the magnesium chloride solution. The purple/brown solution stirred for 16 hours. The solution was vacuum filtered yielding brown filtrate and a small amount of black solid. Solvent was removed from the filtrate under reduced pressure yielding brown solid. $^1$H NMR (DMSO-d$_6$): δ 13.96 (br s; 1 H), 7.05 (br d; J=3.0 Hz; 1 H), 6.53 (dd; J=8.4 Hz, 3.0 Hz; 1 H), 6.42 (br d; J=8.4 Hz; 1 H); 4.29 (s; 2 H).

Preparation of magnesium mesalamine, Mg(mes)$_2$: To a 10-mL round-bottomed flask was added mesalamine (1.00 g, 6.53 mmol). Aqueous sodium hydroxide (1 M, 6.53 ml, 6.53 mmol) was added by pipette and the solid dissolved. To a separate 25-ml round-bottomed flask equipped with magnetic stirrer was added magnesium chloride (310 mg, 3.27 mmol) and water (1 ml). The aqueous mesalamine solution was added by pipette to the magnesium chloride solution. The brown solution was stirred for 16 hours. The solution was vacuum filtered yielding filtrate and a small amount of black solid. Solvent was removed from the filtrate under reduced pressure yielding a dark solid. $^1$H NMR (DMSO-d$_6$): δ 7.04 (br d; J=2.6 Hz; 1 H), 6.51 (br dd; J=8.2 Hz, 2.6 Hz; 1 H), 6.41 (br d; J=8.2 Hz; 1 H); 4.27 (br s; 2 H).

Preparation of barium mesalamine, Ba(mes)$_2$: To a 10-mL round-bottomed flask was added degassed water (6.5 mL) and mesalamine (1.00 g, 6.53 mmol). Barium hydroxide (618 mg, 3.26 mmol) was added and the brown solution was stirred for 16 hours. The solution was vacuum filtered yielding red/brown filtrate and a small amount of dark solid. Solvent was removed from the filtrate under reduced pressure yielding a dark red/brown solid (1.397 g, 96.5%). $^1$H NMR (DMSO-d$_6$): δ 7.03 (br d; J=2.6 Hz; 1 H), 6.53 (br dd; J=8.4 Hz, 2.6 Hz; 1 H), 6.42 (br d; J=8.4 Hz; 1 H).

Preparation of copper mesalamine, Cu(mes)$_2$—Method One: To a 25-mL round-bottomed flask was added mesalamine (1.00 g, 6.53 mmol) and sodium hydroxide (6.53 ml, 6.53 mmol, 1 M) yielding a translucent brown solution. Copper chloride (439 mg, 3.26 mmol) and water were added to a separate flask yielding a translucent green solution. The copper solution was added by pipette to the mesalamine solution, yielding thick black precipitate. The solution was stirred for 16 hours. The solution was vacuum filtered through two pieces of filter paper yielding brown filtrate and black solid. Solvent was removed from the filtrate under reduced pressure yielding brown solid. Precipitate was dried under reduced pressure. NMR data were not collected because copper is paramagnetic.

Preparation of copper mesalamine Cu(mes)$_2$—Method Two: To a 200-mL round-bottomed flask was added mesalamine (1.00 g, 6.53 mmol) and methanol (80 ml). Copper acetate (593 mg, 3.26 mmol) was added forming a green slurry. The green suspension was stirred for 16 hours. The mixture was vacuum filtered yielding blue/green filtrate and black solid. Solvent was removed from the filtrate under reduced pressure and the solid was dried under reduced pressure. NMR data were not collected because copper is paramagnetic.

Preparation of aluminum mesalamine, Al(mes)$_3$: To a 25-mL round-bottomed flask was added mesalamine (1.00 g, 6.53 mmol). An aqueous solution of sodium hydroxide (6.53 ml, 6.53 mmol, 1.0 N) was added in one portion, resulting in a translucent brown solution. Aluminum chloride (4.35 ml, 2.18 mmol, 0.5 M in THF) was added by syringe, forming a thick white precipitate. Water (7 ml) was added to facilitate stirring. The opaque suspension stirred for 16 hours. The mixture was vacuum filtered through filter paper to afford a solid, which was dried under reduced pressure. Yield 0.86 g (94%). $^1$H NMR (DMSO-d$_6$): δ 7.03 (br d; J=2.6 Hz; 1 H), 6.53 (br dd; J=8.4 Hz, 2.6 Hz; 1 H), 6.42 (br d; J=8.4 Hz; 1 H).

Preparation of bismuth mesalamine, Bi(Mes)$_3$: Mesalamine (1.00 g, 6.53 mmol) was added to a 200-mL round-bottomed flask. Anhydrous methanol (80 mL) was added forming a tan slurry. Bismuth acetate (840 mg, 2.18 mmol) was added to the flask. The solution was heated to reflux and stirred for 16 hours. The opaque yellow solution was vacuum filtered yielding a yellow solid, which was dried under reduced pressure and heat. $^1$H NMR (DMSO-d$_6$): δ 7.04 (br s; 1 H), 6.53 (br dd; J=8.8 Hz, 3.2 Hz; 1 H), 6.42 (br s; 1 H).

Synthesis of bismuth mesalamine Phenyl (Bi$_2$mes$_3$(C$_6$H$_5$)): To a glass tube were added mesalamine (200 mg, 1.30 mmol) and DMSO (15 mL). Triphenylbismuth (211 mg, 0.43 mmol) was added to this solution in one portion. The solution was heated to 100° C. for 3 hours then stirred at room temperature for 15 hours. Solvent was removed under reduced pressure leaving a red solid. $^1$H NMR (DMSO-d$_6$): δ 8.78 (d; J=7.8 Hz; 2 H), 7.90 (t; J=7.8 Hz; 2 H), 7.37 (s; 1 H), 7.02 (broad s; 3 H), 6.72 (dd; J=8.2 Hz, 2.6 Hz; 3 H), 6.60 (d; J=8.2 Hz, 3 H). Mesalamine $^1$H NMR (DMSO-d$_6$): δ 7.14 (d; J=2.8 Hz; 1H), 6.86 (dd; J=8.6 Hz, 2.8 Hz; 1H), 6.68 (d; J=8.6 Hz; 1H).

Preparation of Bismuth Subdopate, Bi(O)(dopa): H$_2$O (Baker, Analyzed HPLC grade) was degassed using an aspirator for 4 hours and stored under N$_2$ immediately before use. To a 1000-mL round-bottomed flask equipped with a N$_2$ inlet and magnetic stirrer were added dopaH (2.00 g, 10.2 mmol) and H$_2$O (450 mL). The mixture was gently heated to effect dissolution and, after cooling to room temperature, powdered Bi(OAc)$_3$ (2.00 g, 5.18 mmol) was added in one portion. A yellow precipitate formed almost immediately, and the mixture was stirred at room temperature for 16 hours. The reaction was filtered thru a medium frit and the product was washed with H$_2$O (3×50 mL) to afford a yellow solid. This material was dried under vacuum (25° C., 2 torr) to afford 2.05 g (4.67 mmol, 90%) of Bi(O)(dopa). Approximately 3 mg of this material was dissolved in concentrated HNO$_3$, diluted with H$_2$O (20 mL), and titrated with EDTA (0.001 M) using xylenol orange tetra sodium as an indicator to determine bismuth content. The amount of bismuth found was 50.9% (49.6% based on Bi(O)(dopa)). A sample was submitted for elemental analysis. Found: Bi, 46.8; C, 23.26; H, 2.68; N, 2.71. Calculated: Bi, 47.6; C, 24.61; H, 2.75; N, 3.19. IR (cm$^{-1}$): 3333, 2973, 2901, 1593, 1484, 1407, 1256, 1047. XRD (theta): 8.0, 13.9, 18.4, 20.9, 23.6, 26.6, 31.1, 32.0, 33.0, 36.4, 43.2, 45.9, 46.6, 48.6.

Synthesis of bismuth triiodothyronine: To a 25-mL round-bottomed flask equipped with magnetic stirrer were added sodium T3 (253 mg, 0.376 mmol) and DMSO (15 mL). To this solution was added bismuth nitrate pentahydrate (60.8 mg, 0.125 mmol) in one portion. The solution was stirred for 18 hours at room temperature. Bismuth triiodothyronine was precipitated by the addition of water (120 mL). The tan solid was filtered and washed with water (2×25 mL) and dried under vacuum (50° C., 2 torr) to afford 254 mg (0.12 mmol, 91%) of Bi(C$_{15}$H$_{11}$I$_3$NO$_4$)$_3$. An elemental analysis was obtained. Found: Bi, 8.39; C, 24.34; H, 1.82; N, 2.05. Calculated: Bi, 9.68; C, 25.01; H, 1.67; N, 1.95.

Bioadhesive Polymer Synthetic Protocols: The synthesis of bioadhesive polymers of levodopa and an adjuvant involve chelating several heteroatoms on the polymer to the metal. In the case of alginate, levodopa was loaded 20% by weight and the heteroatom is part of an alcohol functionality or a carboxylate moiety. The option exists with this polymer to allow the carboxylate of alginic acid to participate in charge stabilization of the metal by adding a slight excess of calcium methoxide to produce Ca(dopa)(alginate). Alternatively, excess levodopa is added to the reaction mixture producing Ca(dopa)(alginic acid), in which case the alginic acid is prevented from participating in charge stabilization of the metal. The conditions used to prepare strontium-levodopa-chitin beads were selected such that the nitrogens of chitosan were allowed to chelate with the metal prior to conversion to chitin with the addition of acetic anhydride. Levodopa impregnated beads were prepared as a control for the desorption experiments.

Synthesis of Ca(dopa)(alqinate): To a 100-mL round-bottomed flask equipped with a magnetic stirrer and N$_2$ inlet was added levodopa (100 mg, 0.507 mmol). Water (30 mL) was added and the mixture was heated until the solid dissolved. Calcium methoxide (51.8 mg, 0.52 mmol) was added in one portion. The orange solution was stirred for one hour. Alginic acid (440 mg) was added in one portion and a suspension was formed. The suspension was stirred 12 hours. Solvent was removed under reduced pressure leaving a brown solid.

Synthesis of Ca(dopa)$_2$(alginic acid): To a 100-mL round-bottomed flask equipped with a magnetic stirrer and N$_2$ inlet was added levodopa (100 mg, 0.507 mmol). Water (30 mL) was added and the mixture was heated until the solid dissolved. Calcium methoxide (25.9 mg, 0.26 mmol) was added in one portion. The pale orange solution was stirred for one hour. Alginic acid (440 mg) was added in one portion and a suspension was formed. The suspension was stirred 12 hours. Solvent was removed under reduced pressure leaving a brown solid.

Synthesis of levodopa impregnated Chitin beads: Chitosan (1.00 g, 5.88 mmol) was dissolved in 5% acetic acid (100 mL) with mechanical stirring. Levodopa (115 mg, 0.588 mmol) was added and the solution heated to 40° C. Ethyl acetate (100 mL) was added and the mixture was stirred at 300 rpm, at which time Tween 85 (4.62 mL) was added and the temperature was increased to 45° C. Acetic anhydride (18.2 mL) was added and the mixture was stirred for thirty minutes after which time additional acetic anhydride (18.2 mL) was added and the mixture stirred for 30 minutes until the chitin beads formed. The beads were filtered and washed with water and then methanol. The beads were light grey in color with a uniform spherical shape, approximately 100 μm in diameter. Desorption kinetics (see protocol below) revealed no levodopa released after 18 hours indicating 100% incorporation of levodopa into the chitin beads.

Synthesis of Sr(dopa)$_2$(chitin) beads: To a 100-mL round-bottomed flask equipped with a magnetic stirrer was added chitosan (780 mg). Acetic acid (5%) was added and the mixture stirred until the chitosan dissolved. The solution was then heated to 42° C. and Sr(dopa)$_2$ was added in one portion. Ethyl acetate (78 mL) followed by Tween 85 (3.6 mL) was added and the solution was brought back to 40° C. An aliquot of acetic anhydride (7.1 mL) was added in one portion and the solution stirred for 30 minutes at 300 rpm. Then another aliquot of acetic anhydride (7.1) was added until the chitin beads formed. The beads were filtered through a Buchner funnel and washed with water and methanol.

Method for Rat Pharmacokinetic Studies: Rat "feed and bleed" studies were performed with LD and synthetically prepared LD:metal complexes wherein key PK parameters, such as maximum concentration ($C_{max}$), AUC, and time of maximum concentration ($t_{max}$) were measured vis-à-vis the reference drug, LD.

In each experiment, male Sprague-Dawley rats with jugular vein catheters (250-300 g; n=5-10) are used. These rats were obtained from a commercial source (Harlan Laboratory Animals, Dublin, Va.) and housed individually. Water was available ad libitum. Rats were fed certified rodent chow ad libitum. After arrival, the health of rats was assessed and animals were placed in quarantine for a minimum of five days during which time general health was assessed. At the end of quarantine, rats were moved to permanent animal quarters for access and study.

All studies employed oral dosing using size 9 rodent gelatin capsules from Torpac (Fairfield, N.J.). After fasting overnight, the rats are dosed at time zero with periodic blood sampling from the catheter (5-8 time points between 0 and 24 hours). Blood (200-300 μL) is drawn and collected in heparinized tubes. Plasma is separated by centrifugation and stored at −20° C. until work-up. Plasma samples are then treated according to developed methodology (e.g., *FEBS Lett.*, 2002, 524 (1-3), 199-203), and analyzed (LC/MS/MS) for drug concentrations. Average plasma values (±SEM) for each time are calculated and PK parameters, including $C_{max}$, $t_{max}$, and total amount absorbed ($AUC_{0-6h}$), are determined using standard software.

Each study employs a crossover design whereby the LD and a metal:LD complex are tested in the same rats with a 5-day wash-out period separating the two experiments.

Results are shown in FIGS. 8-15 described below.

Figure 8:
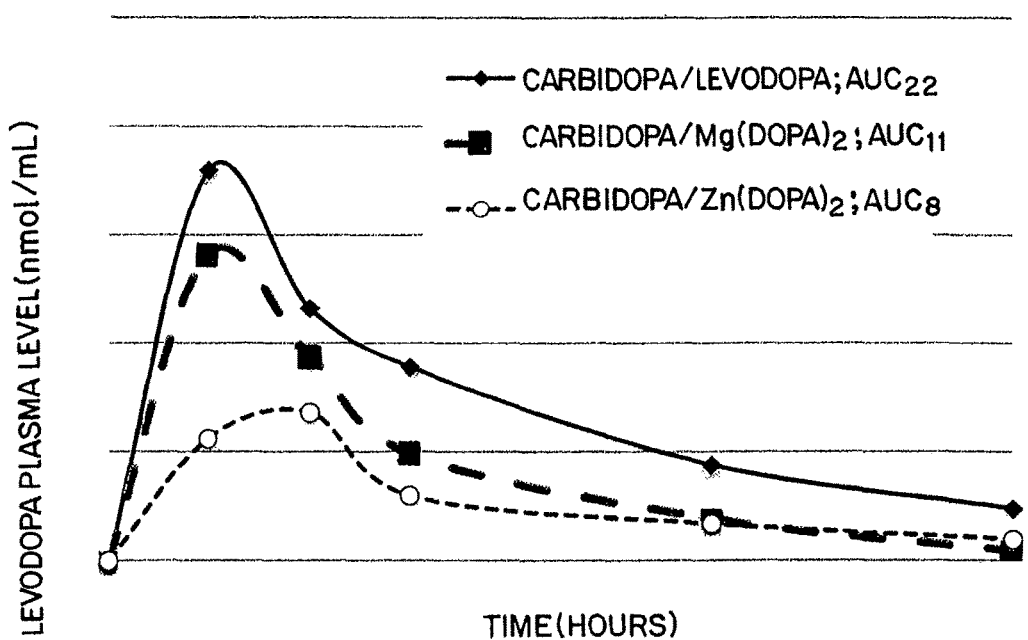
FIG. 8 shows a plot of plasma LD concentration vs. time for carbidopa/LD (a.k.a., dopa), carbidopa/Mg(dopa)$_2$, and carbidopa/Zn(dopa)$_2$.

FIG. 8 shows the plasma level vs. time curves for LD, Mg(dopa)$_2$ and Zn(dopa)$_2$. The data demonstrate that the plasma level-time curves of the metal-complexed LD test drugs were indeed different from LD itself, but the $C_{max}$ values and the AUCs of the metallo-LD compounds were less than that of LD. This demonstrates that merely coordinating LD to a metal does not translate into significant improvement in the plasma level-time curve of LD.

Figure 9:
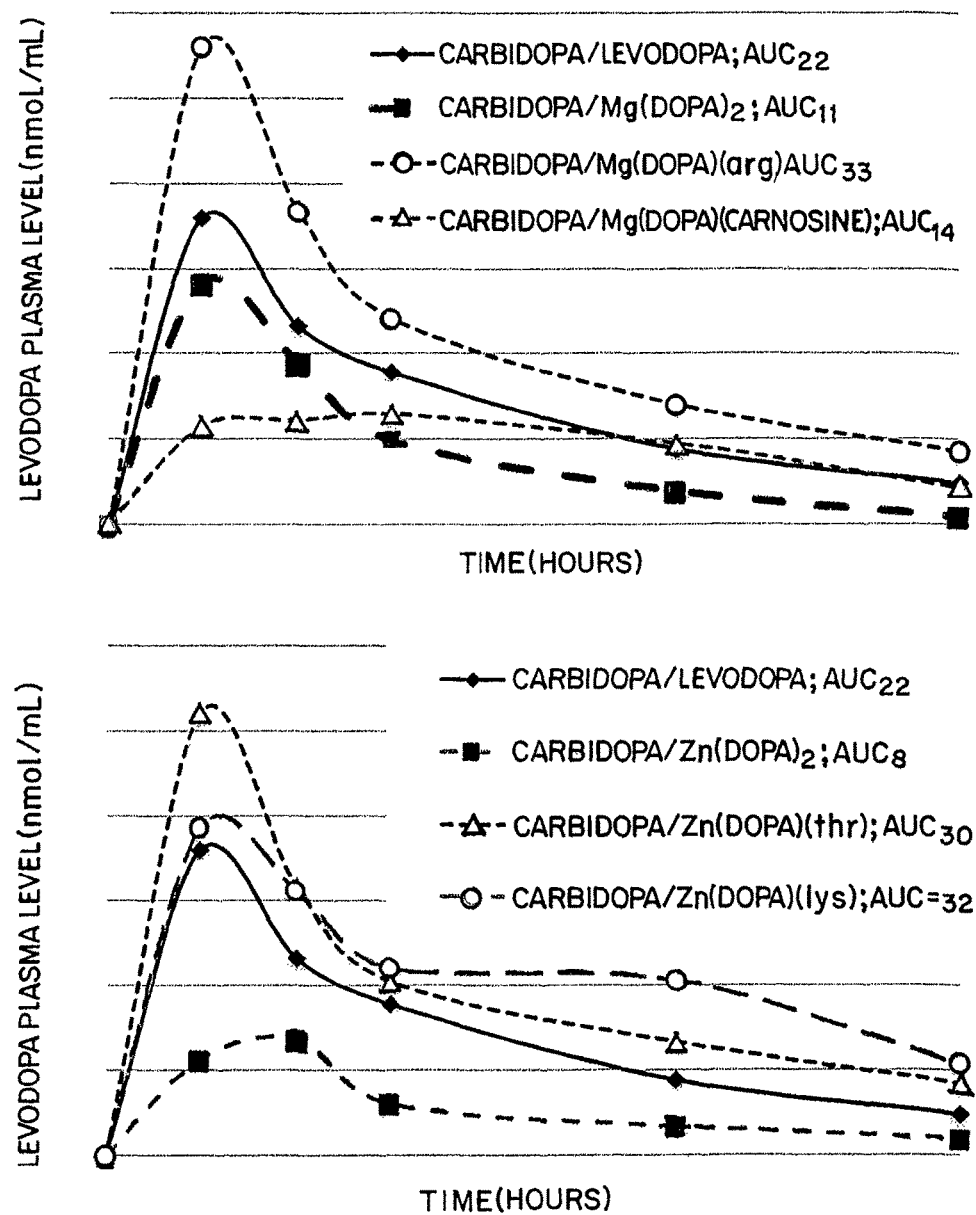
FIG. 9 shows plots of plasma LD concentration vs. time for carbidopa/LD, a series of carbidopa/metal-LD complexes, and a series of carbidopa/metal-LD-adjuvant complexes.

In subsequent rat PK experiments, compounds were tested at an equimolar dosage using LD (10 mg/kg) and a series of metal complexes of LD and adjuvants. The mean values are plotted in each study. FIG. 9 illustrates the results obtained from several complexes of magnesium or zinc with different adjuvants incorporated into the metal-LD coordination complex. Both Zn(dopa)(threonine) and Mg(dopa)(arginine) were absorbed to a greater extent than LD. In order to achieve CDS, however, a plateau of constant LD levels over time is preferrable. The results observed for Zn(dopa)(lysine) and Mg(dopa)(carnosine) suggest this is possible as levels remained relatively steady between 1 and 2 hours. In fact, not only did Zn(dopa)(lysine) reveal favorable a plasma level-time curve for CDS it also exhibited a greater AUC than LD.

Figure 10:
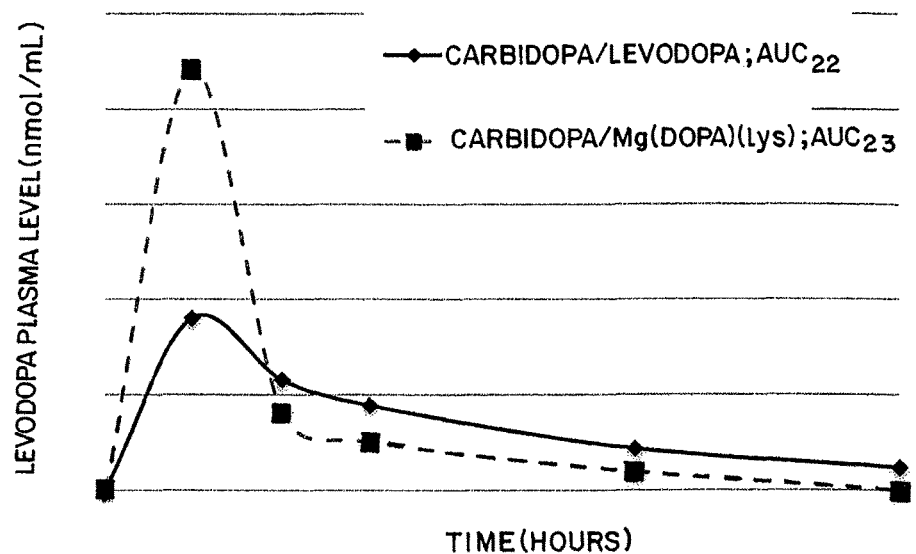
FIG. 10 shows a plot of plasma LD concentration vs. time for carbidopa/LD and carbidopa/Mg(dopa)(lys).

As shown in FIG. 10, a rapid and extensive absorption of LD occurred in the first 40 minutes when Mg(dopa)(lysine) was tested in the rat PK study. This type of plasma level-time curve suggests that such a product would be useful in situations where a fast booster of LD is needed (e.g., in an "off" period prior to the next dose). This complex also illustrates the decreased variability for the Mg(dopa)(lys) complex relative to LD. The $C_{max}$ at 44 μM had a standard deviation (SD) of 3.8 while that of LD was 17 μM with an SD of 9.0.

Figure 11:
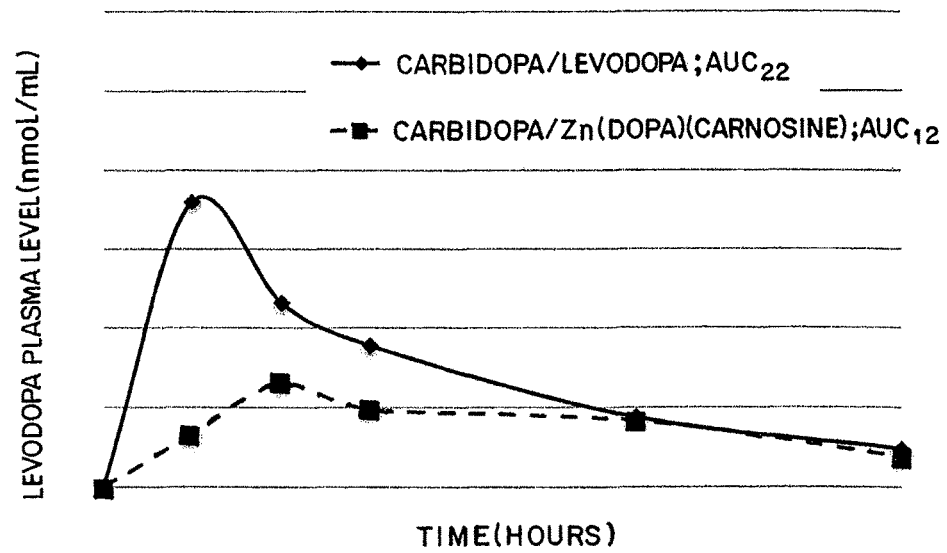
FIG. 11 shows a plot of plasma LD concentration vs. time for carbidopa/LD and carbidopa/Zn(dopa)(carnosine).

As shown in FIG. 11, Zn(dopa)(carnosine) shows the type of curve that suggests a mitigated "pulsatile" character suitable for a LD product better configured to provide CDS. This is similar to the PK profile obseved with Mg(dopa) (carnosine), indicating that carnosine is an adjuvant that imparts extended periods of LD absorption.

Figure 12:
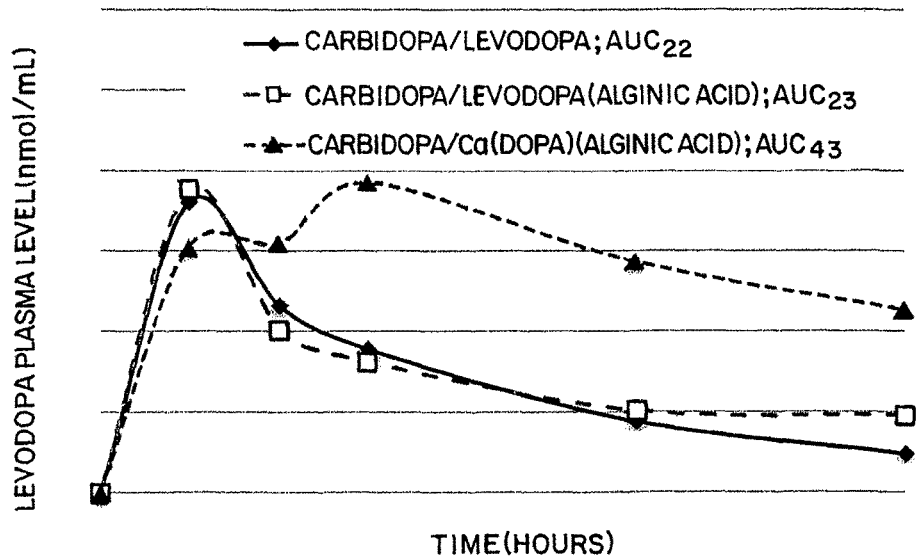
FIG. 12 shows a plot of plasma LD concentration vs. time for carbidopa/LD, carbidopa/dopa(alginic acid), and carbidopa/Ca(dopa)(alginic acid).

The plasma level-time curve of calcium(dopa)(alginate) shown in FIG. 12 is an average over two rat PK studies (i.e., n=10). Orally administering calcium(dopa)(alginate) to rats showed that a therapeutic dose was obtained within 20 minutes. In addition, this compound demonstrated a sustained release profile, and exhibited an AUC greater than or equal to that of LD control. Surprisingly and unexpectedly, in the absence of metal, the sustained release effect is diminished significantly, thereby suggesting that metal complexation serves a key role in extending the absorption phase of LD. The plasma level-time curve observed from the calcium:LD:alginic acid compound represents a potentially favorable plasma level-time curve.

Figure 13:
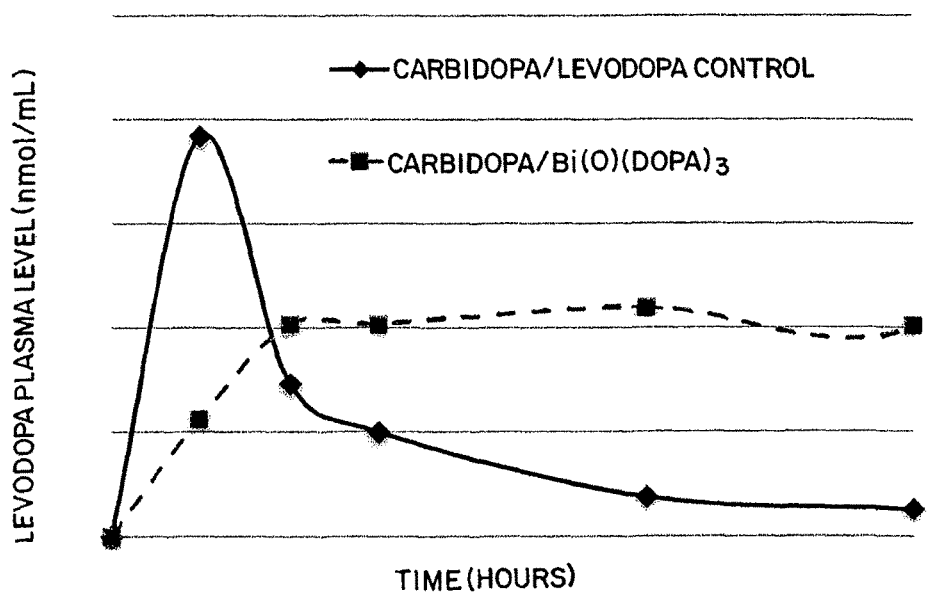
FIG. 13 shows a plot of plasma LD concentration vs. time for a carbidopa/LD control and a carbidopa/Bi(O)(dopa)$_3$ combination.
Figure 14:
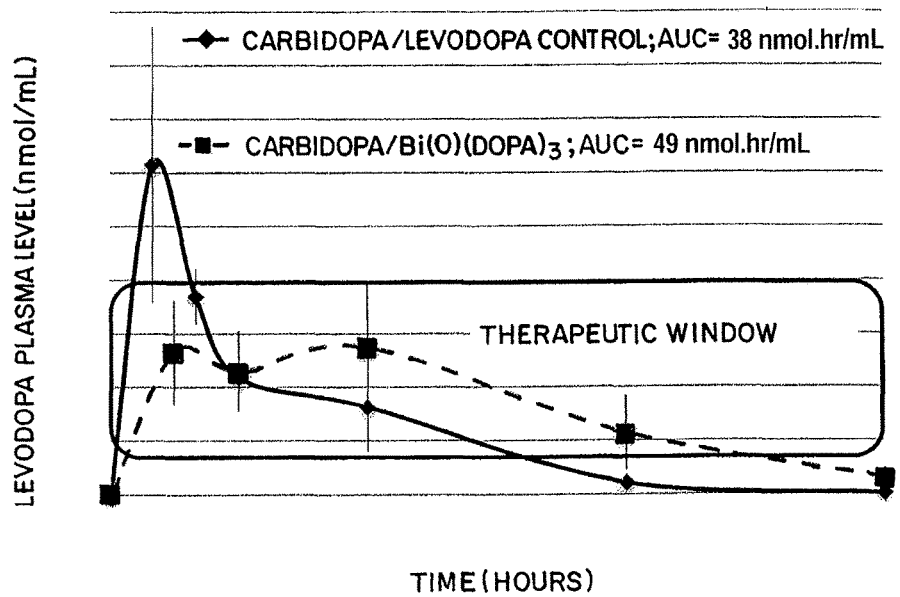
FIG. 14 shows a plot of plasma LD concentration vs. time for a carbidopa/LD control and a carbidopa/Bi(O)(dopa)$_3$ combination in which a portion corresponding to a hypothetical therapeutic window has been indicated.

The plasma level-time curves of LD:bismuth relative to LD control are shown in FIGS. 13 and 14. Doses equivalent to 20 mg/kg of LD in LD-bismuth were orally administered with carbidopa (10 mg/kg) in capsules in both studies. FIG. 13 shows the relative plasma level-time curve when the LD control dose was 10 mg/kg and the carbidopa dose was 5 mg/kg.

It is useful to define a therapeutic window based on minimum and maximum concentrations in human plasma. In clinical practice, it is widely acknowledged that therapeutic concentrations need to be defined individually based on a patient's particular signs and symptoms related to his or her dopaminergic state. However, for the purpose of screening LD products in an animal model, the lower and upper limits are defined broadly to include values applicable to a population of individuals. For this reason, an upper limit defined as the concentration (4 mcg/mL, 20 nmol/mL) below which long-term dyskinesia is not generally observed is used. The lower limit (0.6 mcg/mL, 3 nmol/mL) is the level of LD necessary to avoid "off" times. Thus, the "target range" of LD plasma levels is defined in general terms and should not be confused with individualized determinations that are employed in clinical practice. The present inventors have found that using human-based values of drug concentrations as targets in a rat model is valuable for predicting general clinical performance.

Surprisingly and unexpectedly, as shown in FIG. 13, Bi(O)(dopa)$_3$ has a significantly lower $C_{max}$ than LD despite being administered at twice the dosage. In addition, the LD plasma levels for Bi(O)(dopa)$_3$ remained at or near their peak levels for the duration of the study. The bismuth complex, therefore, renders the drug much more capable of remaining in a given therapeutic window than LD. This improvement is expected to mitigate significantly the potential for dyskinesia and "off" times. Another batch of Bi(O)(dopa)$_3$ was made and tested for comparison with an equimolar dose of LD (i.e., 20 mg/kg). The sampling time was extended from 3 to 6 hours in this study and the plasma level-time curves are shown in FIG. 14. In this experiment, the time following the $t_{max}$ of LD (20 minutes) and the time the LD plasma level falls below the minimum effective clinical plasma level of 3 nmol/mL were followed. As shown in FIG. 14, the data indicate clearly that the time spent in the hypothetical therapeutic window for Bi(O)(dopa)$_3$ is more than that observed for LD/carbidopa. Accordingly, it is expected that the higher LD plasma levels at later time points should translate to a longer clinical duration of action. As in the first set of experiments, Bi(O)(dopa)$_3$ displays a plasma level of 10 nmol/mL at 3 hours, thereby confirming batch-to-batch consistency. Thus, in accordance with the present teachings, a combination of a lower $C_{max}$ and a longer duration of action for Bi(O)(dopa)₃ relative to LD/carbidopa in rats is achieved.

Figure 15:
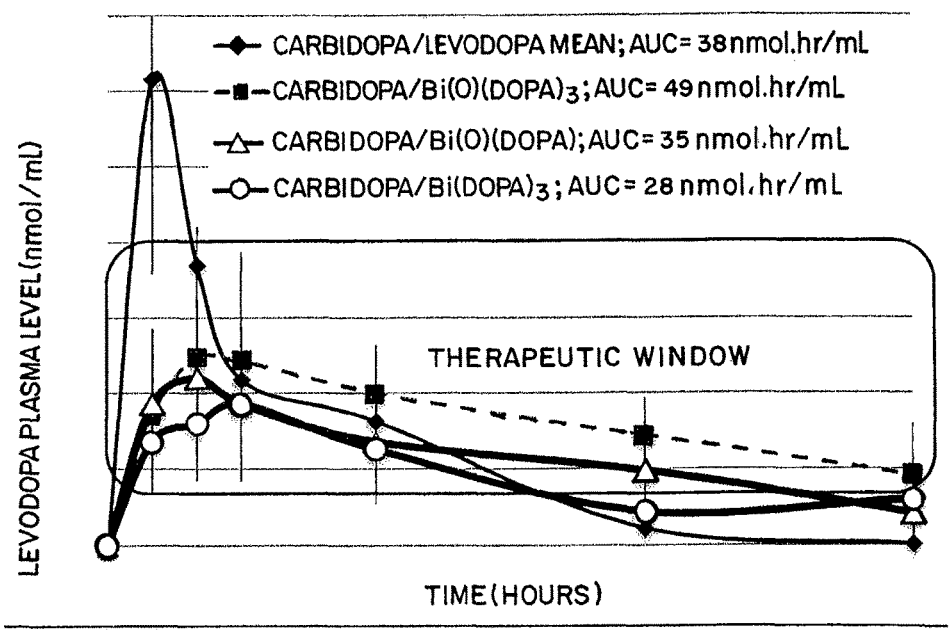
FIG. 15 shows a plot of plasma LD concentration vs. time for a carbidopa/LD control, carbidopa/Bi(dopa)$_3$, carbidopa/Bi(O)(dopa), and carbidopa/Bi(O)(dopa)$_3$ in which a portion corresponding to a hypothetical therapeutic window has been indicated.

In FIG. 15, the plasma level vs. time curves are presented for LD and three different complexes. All three exhibited a significant reduction in $C_{max}$ while both Bi(O)-containing complexes also extended the time spent in the hypothetical therapeutic window.

The foregoing detailed description, examples, and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A compound comprising: bismuth and
a biologically active agent coordinated to the bismuth;
    wherein the biologically active agent comprises at least one heteroatom configured for coordination with the bismuth;
    wherein the biologically active agent is levodopa and wherein the compound is selected from Bi(O)(levodopa) and Bi(O)(levodopa)₃.

2. The compound of claim 1 wherein the biologically active agent and the bismuth are coordinated through a single point of attachment.

3. The invention compound of claim 1 wherein the biologically active agent and the bismuth are coordinated through multiple points of attachment.

4. The compound of claim 1 wherein the compound further comprises an adjuvant coordinated to the bismuth.

5. The compound of claim 1 wherein a pharmacokinetic property of the biologically active agent released from the compound is modulated relative to that of the biologically active agent in an uncoordinated state.

6. The compound of claim 1 wherein the compound further comprises an adjuvant selected from the group consisting of lipids, carbohydrates, amino acids, bioadhesive polymers, peptides, bile acids, and combinations thereof.

7. The compound of claim 6 wherein the adjuvant comprises a carbohydrate.

8. The compound of claim 1 further comprising an adjuvant which is ascorbic acid.

9. The compound of claim 6 wherein the adjuvant is selected from the group consisting of arginine, glycine, leucine, and combinations thereof.

10. The compound of claim 6 wherein the adjuvant is selected from the group consisting of citric acid, carnosine, ferulic acid, alginic acid, sodium alginate, chitosan, chitin, polyacrylic acids, pectin, pullulan, hydroxypropylmethylcellulose, and combinations thereof.

11. The compound of claim 1, wherein the compound is Bi(O)(levodopa).

12. The compound of claim 1, wherein the amount of bismuth in the compound is from about 25% to about 50%.

13. The compound of claim 1, wherein the compound is insoluble in water.

14. The compound of claim 1 made by a process comprising:
    a) providing a solvent comprising water to a reaction chamber;
    b) adding an amount of levodopa to the reaction chamber;
    c) adding an amount of a source of bismuth to the reaction chamber; and
    d) isolating the compound as a solid precipitant.

15. A method of manufacturing a bismuth-containing compound comprising levodopa, carbidopa and combinations thereof comprising:
    a) providing a solvent comprising water to a reaction chamber;
    b) adding an amount of levodopa or carbidopa or a mixture thereof to the reaction chamber;
    c) adding an amount of a source of bismuth to the reaction chamber; and
    d) isolating the compound as a solid precipitant.

16. A bismuth-containing compound made by the method of claim 15.

* * * * *